United States Patent
Greenspan

(10) Patent No.: US 11,771,669 B2
(45) Date of Patent: *Oct. 3, 2023

(54) TOPICAL COMPOSITION AND DELIVERY SYSTEM AND ITS USE

(71) Applicant: SBG MEDICAL TECHNOLOGIES, INC., Dover, DE (US)

(72) Inventor: Michael Harvey Greenspan, Morristown, NJ (US)

(73) Assignee: SBG MEDICAL TECHNOLOGIES, INC., Dover, DE (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/308,692

(22) Filed: May 5, 2021

(65) Prior Publication Data

US 2021/0251926 A1 Aug. 19, 2021

Related U.S. Application Data

(60) Continuation of application No. 16/291,221, filed on Mar. 4, 2019, now Pat. No. 11,026,902, which is a division of application No. 15/014,988, filed on Feb. 3, 2016, now Pat. No. 10,265,283, which is a continuation-in-part of application No. 14/098,633, filed on Dec. 6, 2013, now Pat. No. 10,391,074.

(60) Provisional application No. 61/765,115, filed on Feb. 15, 2013, provisional application No. 61/734,748, filed on Dec. 7, 2012.

(51) Int. Cl.
| | |
|---|---|
| *A61K 31/167* | (2006.01) |
| *A61K 9/00* | (2006.01) |
| *A61K 47/08* | (2006.01) |
| *A61K 47/20* | (2006.01) |
| *A61K 31/196* | (2006.01) |
| *A61K 31/245* | (2006.01) |
| *A61K 31/573* | (2006.01) |
| *A61K 47/10* | (2017.01) |
| *A61P 23/02* | (2006.01) |
| *A61K 31/10* | (2006.01) |
| *A61K 31/08* | (2006.01) |
| *A61K 45/06* | (2006.01) |
| *A61K 9/127* | (2006.01) |

(52) U.S. Cl.
CPC .......... *A61K 31/167* (2013.01); *A61K 9/0014* (2013.01); *A61K 9/127* (2013.01); *A61K 31/08* (2013.01); *A61K 31/10* (2013.01); *A61K 31/196* (2013.01); *A61K 31/245* (2013.01); *A61K 31/573* (2013.01); *A61K 45/06* (2013.01); *A61K 47/08* (2013.01); *A61K 47/10* (2013.01); *A61K 47/20* (2013.01); *A61P 23/02* (2018.01)

(58) Field of Classification Search
CPC .. A61K 31/137; A61K 31/167; A61K 31/245; A61K 47/10; A61K 47/20; A61K 9/0014; A61K 9/127; A61P 23/02
See application file for complete search history.

(56) References Cited

U.S. PATENT DOCUMENTS

| | | |
|---|---|---|
| 48,404,539 | 6/1989 | Guo et al. |
| 5,270,302 A | 12/1993 | Shiosaki et al. |
| 5,650,157 A | 7/1997 | Bockow |
| 5,686,112 A | 11/1997 | Liedtke |
| 5,709,855 A | 1/1998 | Bockow |
| 6,201,022 B1 | 3/2001 | Mease et al. |
| 6,399,039 B2 | 6/2002 | Ostgard |
| 6,416,772 B1 | 7/2002 | Van Engelen et al. |
| 8,420,114 B2 | 4/2013 | Zanella et al. |
| 9,034,298 B2 | 5/2015 | Gruell et al. |
| 10,265,283 B2 | 4/2019 | Greenspan |
| 10,391,074 B2 | 8/2019 | Greenspan |
| 11,026,902 B2 | 6/2021 | Greenspan |
| 2003/0104046 A1 | 6/2003 | Patel |
| 2003/0152637 A1 | 8/2003 | Chasin et al. |
| 2004/0131665 A1 | 7/2004 | Wepfer |
| 2007/0243132 A1 | 10/2007 | Russell-Jones et al. |

(Continued)

FOREIGN PATENT DOCUMENTS

| | | |
|---|---|---|
| WO | 2008079898 A1 | 7/2008 |
| WO | 2010/140170 A1 | 12/2010 |

(Continued)

OTHER PUBLICATIONS

Baumann et al., Safety and efficacy of a rapid-acting topical 4% lidocaine gel in a unique drug delivery system, J of Drugs in Dermatology, 2010, vol. 9, pp. 1500-1504.
Greenblatt et al., Lidodaine plasma concentrations following administration of intraoral lidodaine solution, Arch Otolaryngol, 1985, vol. 111, pp. 298-300.
Ijntama et al. Hydoxypatite microcarriers for biocontrolled release of protein drugs, Int. J of Pharmaceutics, 1994, vol. 111, p. 215-224.
International Preliminary Report on Patentability for PCT/US2016/016517; dated Aug. 7, 2018 (6 pages).

(Continued)

*Primary Examiner* — Theodore R. Howell
(74) *Attorney, Agent, or Firm* — McCarter & English, LLP; Beverly W. Lubit

(57) ABSTRACT

The described invention provides a topical delivery system comprising a pharmaceutical composition for application directly to a skin of a subject in need thereof comprising (a) an effective therapeutic amount of an active therapeutic agent; (b) chemical drivers comprising an amino benzoate local anesthetic, ethoxydiglycol and methylsulfonylmethane (MSM) that in combination are effective to synergistically deliver the therapeutic agent; and (c) a depot component for keeping the pharmaceutical composition in the skin. Methods for delivering an active therapeutic agent into skin, for keeping it in the skin, for reducing systemic side effects attributable to entry of the active agent into the blood stream, and a method for treating a condition, disease or disorder of skin topically also are described in accordance with the embodiments of the described invention.

16 Claims, 7 Drawing Sheets

(56) References Cited

U.S. PATENT DOCUMENTS

| | | |
|---|---|---|
| 2007/0269379 A1 | 11/2007 | Mitragotri et al. |
| 2008/0107747 A1 | 5/2008 | Roederer |
| 2008/0154210 A1 | 6/2008 | Jordan et al. |
| 2010/0055138 A1 | 3/2010 | Margulies et al. |
| 2012/0214874 A1 | 8/2012 | Buyuktimkin et al. |
| 2013/0337031 A1 | 12/2013 | Kisak et al. |
| 2014/0163105 A1 | 6/2014 | Greenspan |
| 2015/0290151 A1 | 10/2015 | Birbara et al. |
| 2016/0151313 A1 | 6/2016 | Greenspan |
| 2019/0374491 A1 | 12/2019 | Greenspan |
| 2021/0015740 A1 | 1/2021 | Greenspan et al. |
| 2023/0210787 A1 | 7/2023 | Greenspan et al. |

FOREIGN PATENT DOCUMENTS

| | | |
|---|---|---|
| WO | 2014089381 A1 | 6/2014 |
| WO | 2014130761 A2 | 8/2014 |
| WO | 2014176417 A1 | 10/2014 |

OTHER PUBLICATIONS

Johnston et al., Sustained delivery of interlukin-2 from a poloxamer 407 gel matrix following intraperitonal injection of mice, Int. J of Pharmaceutics, 1992, vol. 9, pp. 425-434.

Klock et al., Biocompatibility of mannuronic acid-rich alginates, Biomaterials, 1997, vol. 18, pp. 707-713.

Lee et al., Evaluation of chemical enhancers in the transderma delivery of lidocaine, Int. J. of Pharma, 2006, vol. 308, pp. 33-39.

Meier T. et al., Efficacy of Lidocaine path 5% in the treatment of focal . . . , Pain, 2003, vol. 106, pp. 151-158.

Valdes et al., Standards of laboratory practice: cardiac durg monitoring, Clinical Chem, 1998, vol. 44, pp. 1096-1109.

Wayback machine, Apr. 28, 2015, "Neuromed 7 Topical Pain Relief—lidocaine hydrochloride cream", Internet Archive, [online] Available from http s ://web . archive. org/web/20150428014731/ https://dailymed.nlm.nih.gov/dailymed/drugInfo.cfm?setid=f199f56b-d971-4cfB-834d-babb5c2fflla [Accessed Jul. 14, 2021].

Amazon, 2021, "NeuroMed7® 2.2 Ounce Tube", amazon.com, [online] Available from https://www.amazon.com/NeuroMed-7-NeuroMed7-lidocaine-cream/dp/B00T3N1O82 [Accessed Jul. 14, 2021].

International Examination Report for Gt. Britain Application No. 1814047.5, dated Jul. 19, 2021, issued by the International Searching Authority dated Jul. 9, 2021.

U.S. Appl. No. 14/098,633, filed Dec. 6, 2013, U.S. Pat. No. 10,391,074, Granted.

U.S. Appl. No. 16/527,996, filed Jul. 31, 2019, US-2019-0374491-A1, Published.

U.S. Appl. No. 15/014,988, filed Feb. 3, 2016, U.S. Pat. No. 10,265,283, Granted.

U.S. Appl. No. 16/291,221, filed Mar. 4, 2019, U.S. Pat. No. 11,026,902, Granted.

U.S. Appl. No. 17/308,692, filed May 5, 2021, US-2021-0251926-A1, Published.

U.S. Appl. No. 17/036,905, filed Sep. 29, 2020, US-2021-0015740-A1, Published.

Luo, X.; Pietrobon, R.; Sun, S.X.; Liu, G.G.; Hey, L. Estimates and patterns of direct health care expenditures among individuals with back pain in the United States. Spine (Phila. PA 1987) 2004 29(1): 79-86.

Malpass, KG et al. Plst. Reconstr. Surg., Comparison of donor-site healing under Xeroform and Jelonet dressings: unexpected findings, (2003) 112: 430.

Martin, John H. Ch. 23, Receptor Physiology and Submodality Coding in the Somatic Sensory System. In Principles of Neural Science, 2d Ed. Kandel, ER & Schwartz, J:H:, ed. Elsevier, New York, NY; pp. 294-295.

Mehta P et al., (1998). Anesth Prog, Lidocaine toxicity, 45: 38-41.

Moody ML (2010). Topical Medications in the Treatment of Pain. New York City: McMahon Publishing.

Norman, G. et al. Cochrane Database Syst. Rev., Antiseptics for burns, (2017) 7: CD011821.

Osborne DW (2011). J Cosmet Dermatol, Diethylene glycol monoethyl ether: an emerging solvent in topical dermatology products, 10: 324-9.

Otto A et al., (2008). Skin Pharmacol Physiol, Effect of penetration modifiers on the dermal and transdermal delivery of drugs and cosmetic active ingredients, 21: 326-334.

Pacher P et al., 2013. Modulating the endocannabinoid system in human health and disease—successes and failures. FEBS J.280:1918-1943.

Palmieri, TL & Greenhalgh, DG Am. J. Clin. Dermatol., Topical treatment of pediatric patients with burns: a practical guide, (2002)3: 529.

Pazos, MR et al. J. Neuropharmacology, Mechanisms of cannabidiol neuroprotection in hypoxic-ischemic newborn pigs: role of 5HT(1A) and CB2 receptors, (2013) 71: 282.

Physiopedia (https://www.physio-pedia.com/Chronic_Low_Back_Pain).

Ribeiro, A. et al. Eur. J. Pharmacol., Cannabidiol, a non-psychotropic plant-derived cannabinoid, decreases inflammation in a murine model of acute lung injury: role for the adenosine A(2A) receptor, (2012) 678: 78.

Rios, JL J. Ethnopharmacol., Effects of triterpenes on the immune system, (2010) 128: 1-14.

Roberts MS et al., (1999). Inflammopharmacol, Percutaneous absorption of topically applied NSAIDS and other compounds: role of solute properties, skin physiology and delivery systems, 7: 339-50.

Ross, D.A. et al. Br. J. Plast. Surg., The use of cerium nitrate-silver sulphadiazine as a topical burns dressing, (1993) 46: 582.

Rowbotham MC et al., Pain. Lidocaine patch: double-blind controlled study of a new treatment method for post-herpetic neuralgia. Apr. 1996;65(1):39-44. doi: 10.1016/0304-3959(95)00146-8.

Russo EB. 2011. Taming THC: potential cannabis synergy and phytocannabinoid-terpenoid entourage effects. Br J Pharmacol 163(7):1344-64.

Russo EB. 2019. The case for the entourage effect and conventional breeding of clinical cannabis: no "strain," no gain. Front Plant Sci. Jan. 9;9:1969.

Schonfeld, N. Pediatr. Emerg. Care, Outpatient management of burns in children, (1990) 6: 249.

Sleight PJ (1990). Cardiovasc Pharmacol, Medical interventions in acute myocardial infarction, 16: S113-119.

Smoker J, et al.Transdermal lidocaine for perioperative pain: a systematic review of the literature. Curr Pain Headache Rep. Nov. 14, 2019;23(12):89. doi: 10.1007/s11916-019-0830-9.PMID: 31728770.

Stahl, P. H. et al. "Handbook of Pharmaceutical Salts: Properties, Selection, and Use" (Wiley VCH, Zurich, Switzerland: 2002).

Takahashi R et al., (2006). Anesthesiol, Epinephrine increases the extracellular lidocaine concentration in the brain: a possible mechanism for increased central nervous system toxicity, 105: 984-989.

Tenenhaus, M. et al. "Topical agents and dressings for local burn wound care," www.uptodate.com (2020).

Tomko AM et al., Anti-Cancer Potential of Cannabinoids, Terpenes, and Flavonoids Present in Cannabis, Cancers (Basel) 12(7):1985.

Valdes R et al. (1998). Clin Chem, Standards of laboratory practice: cardiac drug monitoring. National Academy of Clinical Biochemistry, 44(5): 1096-1099.

Vloemans, AF et al. Burns, Optimal treatment of partial thickness burns in children: a systematic review, (2014) 40: 177.

Wasiak, J. et al. Cochrane Database Syst. Rev., Dressings for superficial and partial thickness burns, (2008) CD002106.

Wayback machine, Apr. 28, 2015, "Neuromed 7 Topical Pain Relief—lidocaine hydrochloride cream", Internet Archive, [online] Available from http s ://web . archive. org/web/20150428014731/ http <http://archive.org/web/20150428014731/http> s ://dailymed. nlm.nih.gov/dailymed/drugInf<http://dailymed.nlm.nih.gov/dailymed/drugInf> o.cfm?setid=f199f56b-d971-4cf 8-834d-babb5c2fflla [Accessed Jul. 14, 2021].

Webpage printout of https://pubchem.ncbi .nlm .nih .gov/compound/ 1030#section=Structures, accessed Nov. 17, 2022. (Year: 2022).

(56) References Cited

OTHER PUBLICATIONS

Yousefshahi F et al., The efficacy of systemic lidocaine in the management of chronic pain: A Literature Review. J. Anesth Pain Med. Apr. 22, 2017;7(3):e44732. doi: 10.5812/aapm.44732. eCollection Jun. 2017.
Youtube, Nov. 9, 2015, "NeuroMed7 I Topical Anesthetic 1888. 246.6601", youtube.com <http://youtube.com>, [online], Available from NeuroMed7 I Topical Anesthetic 1888.246.6601—YouTube [Accessed Nov. 25, 2021].
Zhang et al., "Assessment of methylsulfonylmethane as a permeability enhancer for regional EDTA chelation therapy"; Drug Delivery; vol. 16; pp. 243-248, 2009.
Alaballa J, Hoffart L. Lidocaine, http://www.lidocaine.weebly.com/references.htm, accessed Aug. 27, 2013.
Amazon, 2021, "NeuroMed7® 2.2 Ounce Tube", amazon.com <http://amazon.com>, [online] Available from <https://www.amazon.com/NeuroMed-7-NeuroMed7-lidocaine-cream/dp/B00T3N1O82> [Accessed Jul. 14, 2021].
Argoff CE et al., (2004). Effectiveness of the lidocaine patch 5% on pain qualities in three chronic pain states: assessment with the Neuropathic Pain Scale. Curr Med Res Opin; 20 Suppl 2:S21-S28. doi:10.1185/030079904X12960.
Becker DE et al., (2012). Anesth Prog, Local anesthetics: review of pharmacological considerations, 59: 90-102.
Ben-Shabat, S. et al. J. Med. Chem., New cannabidiol derivatives: synthesis, binding to cannabinoid receptor, and evaluation of their antiinflammatory activity, (2006) 49: 1113.
Bouchet CA et al., 2020, Cannabinoids in the descending pain modulatory circuit: Role in inflammation. J Pharmacher 2020,107495.
Burstein S, (2015). Cannabidiol (CBD) and its analogs: A review of their effects on inflammation. Bioorganic & Medicinal Chemistry. 23. 10.1016/j.bmc.2015.01.059.
Castillo ER, Lieberman, DE. Lower back pain. Spine 2003, 29, 79-86.
Collinsworth, K. Circulation, The clinical pharmacology of lidocaine as an antiarrhythymic drug, 50: 1217-30 (1974).
Da Cheng Hao, et al. (2015). Ch. 11, in Medicinal Plants; Elsevier, Ltd., pp. 431-464.
Davies et al, 2004;64(9):937-47. doi: 10.2165/00003495-200464090-00002. Review of lidocaine patch 5% studies in the treatment of postherpetic neuralgia.
De Gracia, CG. Burns, An open study comparing topical silver sulfadiazine and topical silver sulfadiazine-cerium nitrate in the treatment of moderate and severe burns, (2001) 27: 67.
Dermal Exposure Assessment: Principles and Applications, EPA/600/8-91/011b, Jan. 1992, Interim Report—Exposure Assessment Group, Office of Health and Environmental Assessment, U.S. Environmental Protection Agency, Washington, D.C. 20460.
Di Marzo, V. "Endocannabinoids' and Other Fatty Acid Derivatives with Cannabimimetic Properties: Biochemistry and Possible Physiopathological Relevance." Biochimica et Biophysica Acta, U.S. National Library of Medicine, Jun. 15, 1998, <https://www.ncbi.nlm.nih.gov/pubmed/9630590>.
Doi et al., 2018, The Japanese Clinical Practice Guideline for acute kidney injury 2016. J of Intensive Care 6,48; doi:10.3390/healthcare6020048S.
Drug Bank. (Feb. 8, 2013). Lidocaine. http:// drugbank.ca/drugs/DB00281, accessed Aug. 28, 2013.
Dunn, K. & Edwards-Jones, V. Burns, The role of Acticoat with nanocrystalline silver in the management of burns, (2004) 30 (1): S1.
Elsohly, MA, Slade, D. Life Sci., Chemical constituents of marijuana: the complex mixture of natural cannabinoids, (2005) 78: 539.
Fichna, J. et al, Neurogastroenterol. Motil., Salvinorin A inhibits colonic transit and neurogenic ion transport in mice by activating kappa-opioid and cannabinoid receptors, (2009) 21: S1326-Se128.
Finlay DB et al., 2020. Terpenoids from cannabis do not mediate an entourage effect by acting at cannabinoid receptors. Front Pharmacol 11:359.
Fortenbach CR, Modjtahedi BS, Maibach HI (2008). Skin Pharmacol Physiol, Role of physical chemical properties in drug relay into skin compartments, 21: 294-299).
Fox, CL et al. Surg. Gynecol. Obstet., Topical chemotherapy for burns using cerium salts and silver sulfadiazine, (1977) 144: 66.
Fults KS, Sustained-Release of Urease from a Poloxamer Gel Matrix, Parent. Set Tech. 44(2):58, 1990.
Gado F, et al. 2020. Modification on the 1,2-dihydro-2-oxo-pyridine-3-carboxamide core to obtain multi-target modulators of endocannabinoid system. Bioorg Chem 94:103353.
Garner, JP & Heppell, PS. Burns, Cerium nitrate in the management of burns, (2005) 31: 539.
Gertsch, J. et al., Anti-inflammatory cannabinoids in diet: Towards a better understanding of CB(2) receptor action? Commun. Integr. Biol. (2008) 1: S26-28.
Gertsch, J. et al., Br. J. Pharmacol., Phytocannabinoids beyond the Cannabis plant—do they exist?, (2010) 160: 523-29.
Gonsiorek W, et al. Mol. Pharmacol., Endocannabinoid 2-Arachidonyl Glycerol Is a Full Agonist through Human Type 2 Cannabinoid Receptor: Antagonism by Anandamide, (2000) 57: 1045-50.
Goodman's & Gilman's The Pharmacological Basis of Therapeutics, Ed. Joel G. Hardman, Lee E. Limbird, Eds., 10th Ed., McGraw Hill, New York (2001), p. 25, 50.
Gregor, C. Chemistry & Physics of Lipids (1993) 64 (1-3): 163-86.
Guindon-Hohmann, AG, Br. J. Pharmacology, Cannabinoid CB2 receptors: a therapeutic target for the treatment of inflammatory and neuropathic pain, (2008) 153: 319-34.
Hansbrough, W. et al. J. Burn Care Rehabil., Management of skin-grafted burn wounds with Xeroform and layers of dry coarse-mesh gauze dressing results in excellent graft take and minimal nursing time, (1995) 16: 531.
Hansen S, Lehr CM, Schaefer UF (2013). Adv Drug Deliv Rev, Improved input parameters for diffusion models of skin absorption, 65: 251-264.
Hashemzadeh H et al., Nature Scientific Reports, Study of Structural stability and formation mechanisms in DSPC and DPSM liposomes: A coarse-grained molecular dynamics simulation, (2020) 10: 183.
Haug, A. et al., Acta Chem. Scand., The influence of pH on the rate of hydrolysis of acidic polysaccharides, 183-90 (1966).
Howlett, AC, et al. Pharmacol. Rev., International Union of Pharmacology. XXVII. Classification of cannabinoid receptors, (2002) 54: 161-202.
http://www.mayomedicallaboratories.com/test-catalog/Clinical+and+Interpretive/8382. Accessed Nov. 19, 2013.
Hughes, J. & Mellows, G. Biochem. J., Inhibition of isoleucyl-transfer ribonucleic acid synthetase in Escherichia coli by pseudomonic acid, (1978) 176: 305.
Inman, RJ et al. Burns Incl. Therm. Inj., Prospective comparison of silver sulfadiazine 1 per cent plus chlorhexidine digluconate 0.2 per cent (Silvazine) and silver sulfadiazine 1 per cent (Flamazine) as prophylaxis against burn wound infection, (1984) 11: 35.
Institute of Medicine of the National Academy of Science. Relieving Pain in America: A Blueprint for Transforming Prevention, Care, Education, and Research; Institute of Medicine: Washington, DC, USA, 2011; p. 5.
Jepps OG, et al. (2013). Adv Drug Deliv Rev, Modeling the human skin barrier—towards a better understanding of dermal absorption, 65: 152-168.
Johnson et al, Safety Assessment of 1,2-Glycols as Used in Cosmetics, International Journal of Toxicology 31 (Supplement 2) 147S-168S, 2012. (Year: 2012).
Katz, J.N. Lumbar disc disorders and low-back pain: Socioeconomic factors and consequences. JBJS 2006, 88, 21-24.
King, AR et al Chem. Biol., Discovery of potent and reversible monoacylglycerol lipase inhibitors, (2009) 16: 1045-52.
Klock, G. et al., "Biocompatibility of mannuronic acid-rich alginates," Biomaterials, vol. 18, No. 10, 707-13 (1997).
Langer, Polymer-Controlled Drug Delivery Systems, Accounts Chem. Res. 26:537, 1993.

(56) References Cited

OTHER PUBLICATIONS

Liu, P. et al., "Metal Chelator combined with permeability enhancer ameliorates oxidative stress-associated neurodegeneration in rat eyes with elevated intraocular pressure," Free Radic. Biol. Med. 69: 289-99 (2014).
Lofgren in 1943 (Lofgren N, Lundqvist B (1946). Svensk Kemisk Tidskrift 58: 206-17.
Lu, H-C, and Mackie, H. Biol. Psychiatry, An introduction to the endogenous cannabinoid system, (2016) 79 (7): 516-25.
Luk, T. et al., Br. J. Pharmacol., Identification of a potent and highly efficacious, yet slowly desensitizing CB1 cannabinoid receptor agonist, (2004) 142: 495-500.
Li et al., Low-level red LED light inhibits hyperkeratinization and inflammation induced by unsaturated fatty acid in an in vitro model mimicking acne. Lasers Surg Med. Feb. 2018;50(2):158-165.
Lister et al., Optical properties of human skin. J Biomed Opt. Sep. 2012;17(9):90901-1, 15 pages.
Lunkenheimer et al., Electromagnetic-radiation absorption by water. Phys Rev E. Dec. 2017;96(6-1):062607, 10 pages.
Machet et al., Phonophoresis: efficiency, mechanisms and skin tolerance. Int J Pharm. Aug. 28, 2002;243(1-2):1-15.
Marovino et al., Iontophoresis in Pain Management. Practical Pain Management. Feb. 21, 2011;8(2):1-19.
Maruani et al., Efficiency of low-frequency ultrasound sonophoresis in skin penetration of histamine: a randomized study in human. Int J Pharm Jan. 29, 2010;385(1-2)37-41.
Matsumura et al. Toxic effects of ultraviolet radiation on the skin. Toxicol Appl Pharmacol. Mar. 15, 2004;195(3):298-308.
Micillo et al., "Fifty Shades" of Black and Red or How Carboxyl Groups Fine Tune Eurnelanin and Pheomelanin Properties. Int J Mol Sci. May 17, 2016;17(5):746, 13 pages.
Mitragotri et al., A mechanistic study of ultrasonically-enhanced transdermal drug delivery. J Pharm Sci. Jun. 1995;84(6):697-706.
Mitragotri et al., Low-frequency sonophoresis: a review. Adv Drug Deliv Rev. Mar. 27, 2004;56(5):589-601.
Mitragotri et al., Ultrasound-mediated transdermal protein delivery. Science. Aug. 11, 1995;269(5225):850-3.
Mitragotri, Devices for overcoming biological barriers: the use of physical forces to disrupt the barriers. Adv Drug Deliv Rev. Jan. 2013;65(1):100-3.
Murthy et al., Magnetophoresis for enhancing transermal drug delivery: Mechanistic studies and patch design. J Control Release. Dec. 1, 2010;148(2):197-203.
Nakagawa et al., In vivo measurement of the water content in the dermis by confocal Roman Spectroscopy. Skin Res Technol. May 2010;16(20):137-41.
Nie et al., Biphasic dose response in the anti-inflammation experiment of PBM. Lasers Med Sci. Feb. 7, 2023;38(1):66, 14 pages.
Ou-Yang et al., Spectral responses of melanin to ultraviolet A irradiation. J Invest Dermatol. Feb. 2004;(2):492-6.
Polat et al., Ultrasound-mediated transdermal drug delivery: mechanisms, scope, and emerging trends. J Control Release. Jun. 30, 2011;152(3):330-48.
Prausinitz et al., Electroporation of mammalian skin: a mechanism to enhance transdermal drug delivery. Proc Natl Acad Sci U S A. Nov. 15, 1993;(22):10504-8.
Prausnitz et al., Skin Barrier and Transdermal Drug Delivery. Dermatology. 2012;3:2065-2073.
Prausnitz et al., Transdermal drug delivery. Nat Biotechnol. Nov. 26, 2008(11):1261-8.
Ramos et al., Characterization of Skeletal Muscle Strain Lesion Induced by Stretching in Rats: Effects of Laser Photobiomodulation. Photomed Laser Surg. Sep. 2018;36(9):460-467.
Randhawa et al., Visble Light Induces Melanogenesis in Human Skin through a Photoadpative Response. PLoS One. Jun. 29, 2015;10(6):e0130949, 14 pages.
Schoellhammer et al., Rapid skin permeabilization by the stimultaneous application of dual-frequency, high-intensity ultrasound. J Control Release. Oct. 28, 2012;163(2):154-60.
Seah et al., Recent advances in ultrasound-based transdermal drug delivery. Int J Nanomedicine. Nov. 20, 2018;13:7749-7763.
Shah et al., Laser treatment of dark skin: an updated review. Am J Clin Dermatol. Dec. 1, 2010;11(6):389-97.
Sites et al., Artifacts and pitfall errors associated with ultrasound-guided regional anesthesia. Part I: understanding the basic principles of ultrasound physics and machine operations. Reg Anesth Pain Med. Sep.-Oct. 2007;32(5):412-8.
Sole et al., Ultrasound approach tracks gut microbes. Nature. Jan. 2018;553(7686):36-37.
Stride et al., Cavitation and contrast: the use of bubbles in ultrasound imaging and therapy. Proc Inst Mech Eng H. 2010;224(2):171-91.
Subramony et al., Microprocessor controlled transdermal drug delivery. Int J Pharm. Jul. 6, 2006;317(1):1-6.
Tachibana, Transdermal delivery of insulin to alloxan-diabetic rabbits by ultrasound exposure. Pharm Res. Jul. 1992;9(7):952-4.
Tomazoni et al., Effects of photobiomodulation therapy and topical non-steroidal anti-inflammatory drug on skeletal muscle injury induced by confusion in rats-part 2: biochemical aspects. Lasers Med Sci. Nov. 2017;32(8):1879-1887.
Wolloch et al., The importance of microject vs shock wave formation in sonophoresis. J Control Release. Dec. 1, 2010;148(2):204-11.
Wong, Electrical, magnetic, photomechanical and cavitational waves to overcome skin barrier for transdermal drug delivery. J Control Release. Nov. 10, 2014;193:257-69.
Wouters et al., Insights into biased signaling at cannabinoid receptors: synthetic cannabinoid receptor agonists. Biochemical Pharmacology. Nov. 2019;169:113623, 15 pages.
Xiao et al., Elucidation of the hierarchical structure of natural eumelanins. J R Soc Interface. Mar. 2018;15(140):20180045.
Young, Chromophores in human skin. Phys Med Biol. May 1997;42(5):789-802.
Yu et al., Enhancing Permeation of Drug Molecules Across the Skin via Delivery in Nanocarriers: Novel Strategies for Effective Transdermal Applications. Front Bioeng Biotechnol. Mar. 29, 2021;6:646554, 17 pages.
Zarghi et al., Selective COX-2 Inhibitors: A Review of Their Structure-Acitivity Relationships. Iran J Pharm Res. 2011 Fall;10(4):655-83.
Zonios et al., Melanin absorption spectroscopy: new method for noninvasive skin investigation and melanoma detection. J Biomed Opt. Jan.-Feb. 2008;13(1):014017, 8 pages.
U.S. Appl. No. 14/098,633, filed Dec. 6, 2013, U.S. Pat. No. 10,391,074, Issued.
U.S. Appl. No. 16/527,996, filed Jul. 31, 2019, 2019-0374491, Published.
U.S. Appl. No. 15/014,988, filed Feb. 3, 2016, U.S. Pat. No. 10,265,283, Issued.
U.S. Appl. No. 16/291,221, filed Mar. 4, 2019, U.S. Pat. No. 11,026,902, Issued.
U.S. Appl. No. 17/036,905, filed Sep. 29, 2020, 2021-0015740, Published.
U.S. Appl. No. 18/119,672, filed Mar. 9, 2023, 2023-0210787, Published.
Abu-Zidan et al., Clinical ultrasound physics. J Emerg Trauma Shock. Oct. 2011;4(4):501-3.
Ahmadi et al., Bio-effects and safety of low-intensity, low-frequency ultrasonic exposure. Pro Biophys Mol Biol. Apr. 2012;108(3):119-38.
Al-Zoubi et al., Structural Insights into CB1 Receptor Biased Signaling. Int J. Mol Sci. Apr. 13, 2019;20(8):1837, 24 pages.
Alexander et al., Approaches for breaking the barriers of drug permeation through transdermal drug delivery. J Control Release. Nov. 28, 2012;164(1):26-40.
Alhasaniah et al., The Impact of Ultraviolet Radiation on Barrier Function in Human Skin: Molecular Mechanisms and Topical Therapeutics. Curr Med Chem. 2018;25(40):5503-5511.
Aliodoust et al., Evaluating the effect of low-level laser therapy on healing of tentomized Achilles tendon in streptozotocin-induced diabetic rats by light microscopical and gene expression examinations. Lasers Med Sci. Jul. 2014;29(4):1495-503.

(56) References Cited

OTHER PUBLICATIONS

Anderson et al., Selective photothermotysis: precise microsuregery by selective absorption of pulsed radiation. Science. Apr. 29, 1983;220(4596):524-7.
Anderson et al., The optics of human skin. J Invest Dermatol. Jul 1981;77(1):13-9.
Ashokkumar, The characterization of acoustics cavitation bubbles—an overview. Ultrason Sonochem. Jul. 2011;18(4):864-72.
Beauchamp et al. Sweat-testing: a review of current technical requirements. Pediatr Pulmonol. Jun. 2005;39(6):507-11.
Bellantone et al., Faster determination of membrane permeabilities without using the lag time method. Int J Pharm. Nov. 6, 2002;248(1-2):81-92. (author listed as Nanda).
Bhatt et al., Laser surgery in dark skin. Dermatol Surg. Feb. 2008;34(2):184-94.
Blue-Emu, Blue, EMU Original Super Strength 2 oz. Retrieved online at: https://www.blue-emu.com/blue-emu-original/blue-emu-original-2-oz. 4 pages, Accessed Jun. 30, 2021.
Boer et al., Structural and biophysical characteristics of human skin in maintaining propert epidermal barrier function. Postephy Dermatol Alergol. Feb. 2016;33(1):1-5.
Brenner et al., The protective role of melanin against UV damage in human sksin. Photochem Photobiol. May-Jun. 2008;84(3):539-49.
Brown et al., Dermal and transdermal drug delivery systems: current and future prospects. Drug Deliv. May-Jun. 2006;13(3):175-87.
Byrne et al., Use of iontrophoresis for the treatment of cancer. J Control Release Aug. 28, 2018;284:144-151.
Cabanero et al., Protective role of neuronal and lymphoid cannabinoid CB2 receptors in neuropathic pain. Elife. Jul. 20, 2020;9:e55582.
Calabrese, Hormesis: Path and Progression to Significance. Int J Mol Sci. Sep. 21, 2018(10):2871, 15 pages.
Castillo et al., The Neuroprotective effect of cannabidiol in an in vitro model of newborn hypoxic-ischemic brain damage in mice is mediated by CB(2) and adenosine receptors. Neurobiol Dis. Feb. 2010;37(2):434-40.
Chen et al., Sonophoretic enhanced microneedles array (SEMA)-Improving the efficiency of transdermal drug delivery. Sensors and Actuators B: Chemical. Mar. 4, 2010;145(1):54-60.
Christensen et al., Ultraviolet Photobiology in Dermatology. Adv Exp Med Biol. 2017;996:89-104.
De Cock et al., Ultrasound and microbubble mediated drug delivery: acoustic pressure as determinant for uptake via membrane pores or endocytosis. J Control Release. Jan. 10, 2015;197-20-8.
De Freitas et al., Proposed Mechanisms of Photobiomodulation or Low-Level Light Therapy. IEEE J Sel Top Quantum Electron. May-Jun. 2016;22(3):7000417, 17 pages.
Denet et al., Skin electroporation for transdermal and topical delivery. Adv Drug Deliv Rev. Mar. 27, 2004;56(5):659-74.
Dhote et al., Iontophoresis: a potential emergence of transdermal drug delivery system. Sci Pharm. Jan.-Mar. 2012;80(1):1-28.
Doukas et al., Transdermal drug delivery with a pressure wave. Adv Drug Deliv Rev. Mar. 27, 2004;56(5):559-79.
Gatchel et al., Transitioning from Acute to Chronic Pain: An Examination of Different Trajectories of Low-Back Pain. Healthcare (Basel). May 17, 2018;6(2):48, 12 pages.
Gordon et al., Current updates of the water-vapor line list in HITRAN: A new "Diet" for air-broadened half-widths. Journal of Quantitative Spectroscopy and Radiative Transfer. Dec. 2007;108(3):389-402.
Guy et al., Iontophoresis: electrorepulsion and electroosmosis. J Control Release. Feb. 14, 2000;64(1-3):129-32.
Haar et al., Ultrasonic imaging: safety considerations. Interface Focus. Aug. 6, 2011;1(4):686-97.
Hamblin, Mechanisms and Mitochondrial Redox Signaling in Photobiomodulation. Photochem Photobiol. Mar. 2018;94(2):199-212.
Hammell et al., Transdermal cannabidiol reduces inflammation and pain-related behaviours in a rat model of arthritis Eur J Pain. Jul. 2016;20(6):936-48.
Huang et al., Biphasic dose response in low level light therapy—an update. Dose Response. 2011;9(4):602-18.
Huang et al., Overcoming ocular drug delivery barriers through the use of physical forces. Adv Drug Deliv Rev. Feb. 15, 2018;126:96-112.
Hunt et al., Eumelanin and phaeomelanin contents of human epidermis and cultured melanocytes. Pigment Cell Res. Aug. 1995;8(4):202-8.
ICNIRP Guidelines on Limits of Exposure to Laser Radiation of Wave Lengths Between 180 nm and 1,000 mm: Erratum. Health Phys. May 2020;118(5):580.
ICNIRP, Infrared Radiation. Retrieved online at: https://www.icnirp.org/en/frequencies/infrared/index/html. 4 pages, (2023).
ICNIRP, International Commission on Non-Ionizing Radiation Protection. ICNIRP Guidelines on Limits of Exposure to Laser Radiation of Wavelengths between 180 nm and 1,000 ?m. Health Phys. Sep. 2013;105(3):271-295.
ITA et al., Recent progress in transdermal sonophoresis. Pharm Dev Technol. Jun. 2017;22(4):458-466.
Jacques, Optical properties of biological tissues: a review. Phys Med Biol. Jun. 7, 2013;58(11):R37-61.
Jain et al., Physics of Ultrasound. Anaesth Pain & Intensive Care. 2015;19(4):533-539.
Karpinski, Selected Medicines Used in Iontophoresis. Pharmaceutics. Oct. 25, 2018;10(4):204, 13 pages.
Kim et al., Forced infiltration of silica beads into densely-packed glass fibre beds for thin composite laminates. RSC Advances. 2016;6(94):91341-91348.
Kreyden et al., Iontophoresis for palmoplantar hyperhidrosis. J Cosmet Dermatol. Dec. 2004;3(4):211-4.
Krishnan et al., Enhanced skin permeation of naltrexone by pulsed electromagnetic fields in human skin in vitro. J Pharm Sci. Jun. 2010;99(6):2724-31.
Kuffler, Photobiomodulation in promoting wound healing: a review. Regen Med. Jan. 2016;11(1):107-22.
Lavon et al., Ultrasound and transdermal drug delivery. Drug Discov Today. Aug. 1, 2004;9(15);670-6.
Lawrence et al., The UV/Visble Radiation Boundary Region (385-405?nm) Damages Skin Cells and Induces "dark" Cyclobutane Pyrimidine Dimers in Human Skin in vivo. Sci Rep. Aug. 24, 2018;8(1):12722, 12 pages.
Lev-Tov et al., Inhibition of fibroblast proliferation in vitro using red light-emitting diodes. Dermatol Surg. Aug. 2013;39(8):1167-70.

TOPICAL COMPOSITION AND DELIVERY SYSTEM AND ITS USE

CROSS-REFERENCE TO RELATED APPLICATIONS

This application is a continuation of U.S. patent application Ser. No. 16/291,221 (filed Mar. 4, 2019), which is a divisional of U.S. patent application Ser. No. 15/014,988 (filed Feb. 3, 2016), which is a continuation-in-part of U.S. application Ser. No. 14/098,633 (filed Dec. 6, 2013), which claims the benefit of priority to provisional application 61/734,748 (filed Dec. 7, 2012) and 61/765,115 (filed Feb. 15, 2013). Each of these applications is incorporated herein by reference in its entirety.

FIELD OF THE INVENTION

The described invention relates to topical formulations of a pharmaceutical compositions containing an active therapeutic agent or metabolite, and a delivery system for administering the same topically, characterized in that the active(s) remain in the skin and penetration of the active(s) into the bloodstream is limited so as to reduce systemic side effects.

BACKGROUND OF THE INVENTION

1. Anatomy and Physiology of the Skin

The skin is the largest organ in the body consisting of several layers and plays an important role in biologic homeostasis, and is comprised of the epidermis and the dermis. The epidermis, which is composed of several layers beginning with the stratum corneum, is the outermost layer of the skin, and the innermost skin layer is the deep dermis. The skin has multiple functions, including thermal regulation, metabolic function (vitamin D metabolism), and immune functions. FIG. 1 presents a diagram of skin anatomy.

In humans, the usual thickness of the skin is from 1-2 mm, although there is considerable variation in different parts of the body. The relative proportions of the epidermis and dermis also vary, and a thick skin is found in regions where there is a thickening of either or both layers. For example, on the interscapular (between the shoulder blades) region of the back, where the dermis is particularly thick, the skin may be more than 5 mm thick, whereas on the eyelids it may be less than 0.5 mm. Generally, the skin is thicker on the dorsal or extensor surfaces of the body than on the ventral or flexor surfaces; however, this is not the case for the hands and feet. The skin of the palms and soles is thicker than on any dorsal surface except the intrascapular region. The palms and soles have a characteristically thickened epidermis, in addition to a thick dermis.

The entire skin surface is traversed by numerous fine furrows, which run in definite directions and cross each other to bound small rhomboid or rectangular fields. These furrows correspond to similar ones on the surface of the dermis so that, in section, the boundary line between epidermis and dermis appears wavy. On the thick skin of the palms and soles, the fields form long, narrow ridges separated by parallel coursing furrows, and in the fingertips these ridges are arranged in the complicated loops, whorls (verticil) and spirals that give the fingerprints characteristic for each individual. These ridges are more prominent in those regions where the epidermis is thickest.

Where there is an epidermal ridge externally there is a corresponding narrower projection, called a "rete peg," on the dermal surface. Dermal papillae on either side of each rete peg project irregularly into the epidermis. In the palms and soles, and other sensitive parts of the skin, the dermal papillae are numerous, tall and often branched, and vary in height (from 0.05 mm to 0.2 mm). Where mechanical demands are slight and the epidermis is thinner, such as on the abdomen and face, the papillae are low and fewer in number.

Epidermis

The epidermis provides the body's buffer zone against the environment. It provides protection from trauma, excludes toxins and microbial organisms, and provides a semi-permeable membrane, keeping vital body fluids within the protective envelope. Traditionally, the epidermis has been divided into several layers, of which two represent the most significant ones physiologically. The basal-cell layer, or germinative layer, is of importance because it is the primary source of regenerative cells. In the process of wound healing, this is the area that undergoes mitosis in most instances. The upper epidermis, including stratum and granular layer, is the other area of formation of the normal epidermal-barrier function.

Stratum Corneum and the Acid Mantle

Stratum corneum is an avascular, multilayer structure that functions as a barrier to the environment and prevents transepidermal water loss. Recent studies have shown that enzymatic activity is involved in the formation of an acid mantle in the stratum corneum. Together, the acid mantle and stratum corneum make the skin less permeable to water and other polar compounds, and indirectly protect the skin from invasion by microorganisms. Normal surface skin pH is between 4 and 6.5 in healthy people; it varies according to area of skin on the body. This low pH forms an acid mantle that enhances the skin barrier function.

Other Layers of the Epidermis

Other layers of the epidermis below the stratum corneum include the stratum lucidum, stratum granulosum, stratum germinativum, and stratum basale. Each contains living cells with specialized functions (FIG. 2). For example melanin, which is produced by melanocytes in the epidermis, is responsible for the color of the skin. Langerhans cells are involved in immune processing.

Dermal Appendages

Dermal appendages, which include hair follicles, sebaceous and sweat glands, fingernails, and toenails, originate in the epidermis and protrude into the dermis hair follicles and sebaceous and sweat glands contribute epithelial cells for rapid reepithelialization of wounds that do not penetrate through the dermis (termed partial-thickness wounds). The sebaceous glands are responsible for secretions that lubricate the skin, keeping it soft and flexible. They are most numerous in the face and sparse in the palm of the hands and soles of the feet. Sweat gland secretions control skin pH to prevent dermal infections. The sweat glands, dermal blood vessels, and small muscles in the skin (responsible for goose pimples) control temperature on the surface of the body. Nerve endings in the skin include receptors for pain, touch, heat, and cold. Loss of these nerve endings increases the risk for skin breakdown by decreasing the tolerance of the tissue to external forces.

The basement membrane both separates and connects the epidermis and dermis. When epidermal cells in the basement membrane divide, one cell remains, and the other migrates through the granular layer to the surface stratum corneum. At the surface, the cell dies and forms keratin. Dry keratin on the surface is called scale. Hyperkeratosis (thickened layers of keratin) is found often on the heels and indicates loss of sebaceous gland and sweat gland functions if the patient is diabetic. The basement membrane atrophies with aging; separation between the basement membrane and dermis is one cause for skin tears in the elderly.

Dermis

The dermis, or the true skin, is a vascular structure that supports and nourishes the epidermis. In addition, there are sensory nerve endings in the dermis that transmit signals regarding pain, pressure, heat, and cold. The dermis is divided into two layers: the superficial dermis and the deep dermis.

The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin that give it turgor. Fibronectin and hyaluronic acid are secreted by the fibroblasts. The structural integrity of the dermis plays a role in the normal function and youthful appearance of the skin.

The deep dermis is located over the subcutaneous fat; it contains larger networks of blood vessels and collagen fibers to provide tensile strength. It also consists of fibroelastic connective tissue, which is yellow and composed mainly of collagen. Fibroblasts are also present in this tissue layer. The well-vascularized dermis withstands pressure for longer periods of time than subcutaneous tissue or muscle. The collagen in the skin gives the skin its toughness. Dermal wounds, e.g., cracks or pustules, involve the epidermis, basal membrane, and dermis. Typically, dermal injuries heal rapidly.

2. Effects of Application to the Skin

Substances are applied to the skin to elicit one or more of four general effects: an effect on the skin surface, an effect within the stratum corneum; an effect requiring penetration into the epidermis and dermis; or a systemic effect resulting from delivery of sufficient amounts of a given substance through the epidermis and the dermis to the vasculature to produce therapeutic systemic concentrations. One example of an effect on the skin surface is formation of a film. Film formation may be protective (e.g., sunscreen) and/or occlusive (e.g., to provide a moisturizing effect by diminishing loss of moisture from the skin surface). One example of an effect within the stratum corneum is skin moisturization; which may involve the hydration of dry outer cells by surface films or the intercalation of water in the lipid-rich intercellular laminae; the stratum corneum also may serve as a reservoir phase or depot wherein topically applied substances accumulate due to partitioning into, or binding with, skin components.

It generally is recognized that short-term penetration occurs through the hair follicles and the sebaceous apparatus of the skin, while long term penetration occurs across cells. Penetration of a substance into the viable epidermis and dermis may be difficult to achieve, but once it has occurred, the continued diffusion of the substance into the dermis is likely to result in its transfer into the microcirculation of the dermis and then into the general circulation. It is possible, however, to formulate delivery systems that provide substantial localized delivery.

Percutaneous absorption is the absorption of substances from outside the skin to positions beneath the skin, including into the blood stream. The epidermis of human skin is highly relevant to absorption rates. Passage through the stratum corneum marks the rate-limiting step for percutaneous absorption. The major steps involved in percutaneous absorption of, for example, a drug, include the establishment of a concentration gradient, which provides a driving force for drug movement across the skin, the release of drug from the vehicle into the skin-partition coefficient and drug diffusion across the layers of the skin-diffusion coefficient. The relationship of these factors to one another is summarized by the following equation:

$$J = Cveh \times Km \cdot D/x \qquad \text{[Formula 1]}$$

where J=rate of absorption; Cveh=concentration of drug in vehicle; Km=partition coefficient; and D=diffusion coefficient.

The many factors that affect the rate of percutaneous absorption of a substance include, without limitation, the following: (i) Concentration. The more concentrated the substance, the greater the absorption rate. (ii) Size of skin surface area. The wider the contact area of the skin to which the substance is applied, the greater the absorption rate. (iii) Anatomical site of application. Skin varies in thickness in different areas of the body. A thicker and more intact stratum corneum decreases the rate of absorbency of a substance. The stratum corneum of the facial area is much thinner than, for example, the skin of the palms of the hands. The facial skin's construction and the thinness of the stratum corneum provide an area of the body that is optimized for percutaneous absorption to allow delivery of active agents both locally and systemically through the body. (iv) Hydration. Hydration (meaning increasing the water content of the skin) causes the stratum corneum to swell which increases permeability. (v) Skin temperature. Increased skin temperature increases permeability. (vi) Composition. The composition of the compound and of the vehicle also determines the absorbency of a substance.

Most substances applied topically are incorporated into bases or vehicles. The vehicle chosen for a topical application will greatly influence absorption, and may itself have a beneficial effect on the skin. Factors that determine the choice of vehicle and the transfer rate across the skin are the substance's partition coefficient, molecular weight and water solubility. The protein portion of the stratum corneum is most permeable to water soluble substances and the lipid portion of the stratum corneum is most permeable to lipid soluble substances. It follows that substances having both lipid and aqueous solubility may traverse the stratum corneum more readily. (See Dermal Exposure Assessment: Principles and Applications, EPA/600/8-91/011b, January 1992, Interim Report—Exposure Assessment Group, Office of Health and Environmental Assessment, U.S. Environmental Protection Agency, Washington, D.C. 20460).

3. Wound Healing

The term "wound healing" refers to the process by which the body repairs trauma to any of its tissues, especially those caused by physical means and with interruption of continuity. The term "wound healing agent" refers to any substance that facilitates the wound healing process.

A wound-healing response often is described as having three distinct phases-injury, inflammation and repair. Generally speaking, the body responds to injury with an inflammatory response, which is crucial to maintaining the health and integrity of an organism. If however it goes awry, it can result in tissue destruction.

Phase I: Injury

Injury caused by factors including, but not limited to, autoimmune or allergic reactions, environmental particulates, infection or mechanical damage often results in the disruption of normal tissue architecture, initiating a healing response. Damaged epithelial and endothelial cells must be replaced to maintain barrier function and integrity and prevent blood loss, respectively. Acute damage to endothelial cells leads to the release of inflammatory mediators and initiation of an anti-fibrinolytic coagulation cascade, temporarily plugging the damaged vessel with a platelet and fibrin-rich clot.

Platelet recruitment, degranulation and clot formation rapidly progress into a phase of vasoconstriction with increased permeability, allowing the extravasation (movement of white blood cells from the capillaries to the tissues surrounding them) and direct recruitment of leukocytes to the injured site. The basement membrane, which forms the extracellular matrix underlying the epithelium and endothelium of parenchymal tissue, precludes direct access to the damaged tissue. To disrupt this physical barrier, zinc-dependent endopeptidases, also called matrix metalloproteinases (MMPs), cleave one or more extracellular matrix constituents allowing extravasation of cells into, and out of, damaged sites. Specifically, MMP-2 (gelatinase A, Type N collagenase) and MMP-9 (gelatinase B, Type IV collagenase) cleave type N collagens and gelatin, two important constituents of the basement membrane. Recent studies have found that MMP-2 and MMP-9 are upregulated, highlighting that tissue-destructive and regenerative processes are common in fibrotic conditions. The activities of MMPs are controlled by several mechanisms including transcriptional regulation, proenzyme regulation, and specific tissue inhibitors of MMPs. The balance between MMPs and the various inhibitory mechanisms can regulate inflammation and determine the net amount of collagen deposited during the healing response.

Phase II: Inflammation

Once access to the site of tissue damage has been achieved, chemokine gradients recruit inflammatory cells. Neutrophils, eosinophils, lymphocytes, and macrophages are observed at sites of acute injury with cell debris and areas of necrosis cleared by phagocytes.

The early recruitment of eosinophils, neutrophils, lymphocytes, and macrophages providing inflammatory cytokines and chemokines can contribute to local TGF-β and IL-13 accumulation. Following the initial insult and wave of inflammatory cells, a late-stage recruitment of inflammatory cells may assist in phagocytosis, in clearing cell debris, and in controlling excessive cellular proliferation, which together may contribute to normal healing. Late-stage inflammation may serve an anti-fibrotic role and may be required for successful resolution of wound-healing responses. For example, a late-phase inflammatory profile rich in phagocytic macrophages, assisting in fibroblast clearance, in addition to IL-10-secreting regulatory T cells, suppressing local chemokine production and TGF-β, may prevent excessive fibroblast activation.

The nature of the insult or causative agent often dictates the character of the ensuing inflammatory response. For example, exogenous stimuli like pathogen-associated molecular patterns (PAMPs) are recognized by pathogen recognition receptors, such as toll-like receptors and NOD-like receptors (cytoplasmic proteins that have a variety of functions in regulation of inflammatory and apoptotic responses), and influence the response of innate cells to invading pathogens. Endogenous danger signals also can influence local innate cells and orchestrate the inflammatory cascade.

The nature of the inflammatory response dramatically influences resident tissue cells and the ensuing inflammatory cells. Inflammatory cells themselves also propagate further inflammation through the secretion of chemokines, cytokines, and growth factors. Many cytokines are involved throughout a wound-healing and fibrotic response, with specific groups of genes activated in various conditions.

Phase III: Tissue Repair and Contraction

The closing phase of wound healing consists of an orchestrated cellular re-organization guided by a fibrin (a fibrous protein that is polymerized to form a "mesh" that forms a clot over a wound site)-rich scaffold formation, wound contraction, closure and re-epithelialization. The vast majority of studies elucidating the processes involved in this phase of wound repair have come from dermal wound studies and in vitro systems.

Myofibroblast-derived collagens and smooth muscle actin (α-SMA) form a provisional extracellular matrix, with macrophage, platelet, and fibroblast-derived fibronectin forming a fibrin scaffold. Collectively, these structures are commonly referred to as granulation tissues.

In addition to fibronectin, the provisional extracellular matrix consists of glycoproteins (such as PDGF), glycosaminoglycans (such as hyaluronic acid), proteoglycans and elastin. Growth factor and TGF-β-activated fibroblasts migrate along the extracellular matrix network and repair the wound. Within skin wounds, TGF-β also induces a contractile response, regulating the orientation of collagen fibers. Fibroblast to myofibroblast differentiation, as discussed above, also creates stress fibers and the neo-expression of α-SMA, both of which confer the high contractile activity within myofibroblasts. The attachment of myofibroblasts to the extracellular matrix at specialized sites called the "fibronexus" or "super mature focal adhesions" pull the wound together, reducing the size of the lesion during the contraction phase. The extent of extracellular matrix laid down and the quantity of activated myofibroblasts determines the amount of collagen deposition. To this end, the balance of matrix metalloproteinases (MMPs) to tissue inhibitor of metalloproteinases (TIMPs) and collagens to collagenases vary throughout the response, shifting from pro-synthesis and increased collagen deposition towards a controlled balance, with no net increase in collagen. For successful wound healing, this balance often occurs when fibroblasts undergo apoptosis, inflammation begins to subside, and granulation tissue recedes, leaving a collagen-rich lesion. From skin studies, re-epithelialization of the wound site re-establishes the barrier function and allows encapsulated cellular re-organization. Several in vitro and in vivo models, using human or rat epithelial cells grown over a collagen matrix, or tracheal wounds in vivo, have been used to identify significant stages of cell migration, proliferation, and cell spreading. Rapid and dynamic motility and proliferation, with epithelial restitution from the edges of the denuded area occur within hours of the initial wound. In addition, sliding sheets of epithelial cells can migrate over the injured area assisting wound coverage. Several factors have been shown to regulate re-epithelialization, including serum-derived transforming growth factor alpha (TGF-α), and matrix metalloproteinase-7 (MMP-7) (which itself is regulated by TIMP-1).

4. Delivery Systems for Topical Administration

Many active agents are administrated enterally or parenterally. Enteral routes of administration involve administration to any part of the gastrointestinal tract, typically via oral forms, e.g., pills, tablets, emulsions, and syrups, or via rectal forms, e.g., enemas, Murphy drips, and suppositories. Parenteral routes of administration involve administration by some means other than oral or rectal, typically via injection. While such administration routes allow for accurate and consistent dosing, such routes necessarily yield systemic effects, e.g., vestibular symptoms, headache and general malaise, and gastrointestinal symptoms, which in certain circumstances are not desirable.

Topical routes of administration involve administration to a body surface, such as the skin, or mucous membranes. Many forms of topical administration involve applying a therapeutic agent directly to the skin; inhalable mediations, eye drops, and ear-drops also are considered topical administration forms. Although topical administration generally provides a local effect, many topically administered drugs likewise can exhibit systemic effects, such as vestibular symptoms (e.g., vertigo, dizziness or blurred vision), headache and general malaise, gastro-intestinal symptoms, such as diarrhea, nausea, gas, cramps, dry nose and dry mouth.

Formulations for topical application can take the compositional form of a liquid, a semisolid dosage form (e.g., a paste, a cream, a lotion, a powder, an ointment or a gel) or a patch.

Liquid formulations do not readily stay in place and can be messy. Semisolid formulations offer some advantages characteristic of topical administration, such as ease of application, and increased local doses of active agent, with reduced systemic effects, but their potential disadvantages include the need for repeated application, difficulties in accurate dosing, and messy or unattractive cosmetic attributes, all of which can lead to poor user compliance, and unintentional removal or transfer of active agent via contact with objects or other persons.

Topical patches, which are available in multiple forms including single and multi-layer drug-in-adhesive forms, matrix forms, and reservoir forms, address several of the shortcomings of semisolid formulations, for example, reducing the need for repeated application, providing accurate, and controlled release of active agent, and reducing the likelihood of unintentional removal or transfer of drug or active agent via contact with objects or other persons, but have a finite size and shape. Because topical patches have a finite size and shape, the application area is determined by the dimensions of the patch rather than the dimensions of the affected site. Accordingly, it may be necessary to use a number of patches in order to cover a large affected site. Furthermore, topical patches typically lack sufficient flexibility to be effectively administered to joints or other areas of skin subject to significant stretching movements. Topical patches can also lead to user discomfort, particular in warmer climates, and can be aesthetically unpleasing, which can also lead to poor user compliance.

A number of attempts have been made for delivering therapeutic formulations topically. One common problem inherent to topical formulations that has been experienced thus far has been to control the therapeutic active agent, as well as the other composition components, such that they are specifically confined in the area of the skin in which they have been directly applied. This is turn may result in too fast release of the drug with the consequence of causing undesirable spikes and high levels of the drug in the bloodstream, thereby creating deleterious effects such as e.g. unwanted side-effects, wash-out or metabolism of the drug.

The described invention addresses and overcomes these shortcomings. The described composition and method provides a safe and effective topical therapeutic drug delivery platform that can deliver drugs locally into the skin. The described invention is effective to deliver the components of the pharmaceutical formulation into the skin, to keep them in the skin, and to reduce the potential of the active therapeutic agent or its metabolites to enter the bloodstream. Consequently, the active therapeutic agent executes its effective biological function locally at the tissue of interest once being released from the skin.

SUMMARY OF THE INVENTION

According to one aspect, the described invention provides a topical delivery system comprising a pharmaceutical composition for application directly to a skin of a subject in need thereof comprising (a) a therapeutic amount of an active therapeutic agent to treat symptoms of a disease, disorder or condition; (b) chemical drivers comprising an amino benzoate local anesthetic, ethoxydiglycol and methylsulfonylmethane, wherein the chemical drivers are effective at acting synergistically to deliver the therapeutic agent and (c) a depot component that is effective to keep the active agent locally in the skin; reduce distribution of the active agent to the blood stream; to encapsulate the pharmaceutical composition and to facilitate controlled or delayed type release of the active therapeutic agent. According to some embodiments, the active therapeutic agent has a molecular weight below 500 Da. According to some embodiments, the active therapeutic agent is selected from the group consisting of a steroidal or non-steroidal analgesic agent, a wound healing agent, an antihistamine and an anti-neoplastic agent. According to some embodiments the amino benzoate local anesthetic is selected from the group consisting of benzocaine, lidocaine, tetracaine or a combination thereof. According to some embodiments, the pharmaceutical composition is in an administration form selected from the group consisting of a cream, gel, or a spray. According to some embodiments, the topical delivery system further comprises a vasoconstrictor. According to some embodiments, the vasoconstrictor is nonirritating when applied to skin. According to some embodiments, the depot component is a liposome. According to some embodiments, the liposome comprises a phosphatidyl choline, cholesterol, and a pharmaceutically acceptable salt of an active therapeutic agent and at least one anionic or cationic phospholipid. According to some embodiments, the depot component comprises a polymer. According to some embodiments, the depot component comprises a liposome and a polymer. According to some embodiments, the depot component comprises a polymersome.

According to another aspect, the described invention provides a method of delivering a pharmaceutical composition topically that is effective to reduce systemic side effects of the active agent comprising (a) applying a pharmaceutical composition to a skin of a subject in need thereof, wherein the pharmaceutical composition comprises: (i) a chemical driver effective to penetrate the stratum corneum of skin containing an active therapeutic agent, wherein the active therapeutic agent is an amino benzoate local anesthetic; ethoxydiglycol and methylsulfonylmethane (MSM); and (ii) a depot component that is effective to keep the pharmaceutical composition in the skin and to minimize distribution systemically. According to some embodiments, the active therapeutic agent has a molecular weight below 500 Da. According to some embodiments, the active therapeutic agent does not get into the bloodstream. According to some embodiments, the depot component of the composition is effective to facilitate controlled or delayed type release of the active therapeutic agent. According to some embodiments, the depot component is a polymer. According to other embodiments, the depot component is a liposome. According to some embodiments, the liposome comprises a phosphatidyl choline, cholesterol and a pharmaceutically acceptable salt of an active therapeutic agent and at least one anionic or cationic phospholipid. According to some embodiments, the depot component comprises a liposome and a polymer. According to other embodiments, the depot component is a polymersome.

DETAILED DESCRIPTION OF THE INVENTION

Glossary

Figure 1:
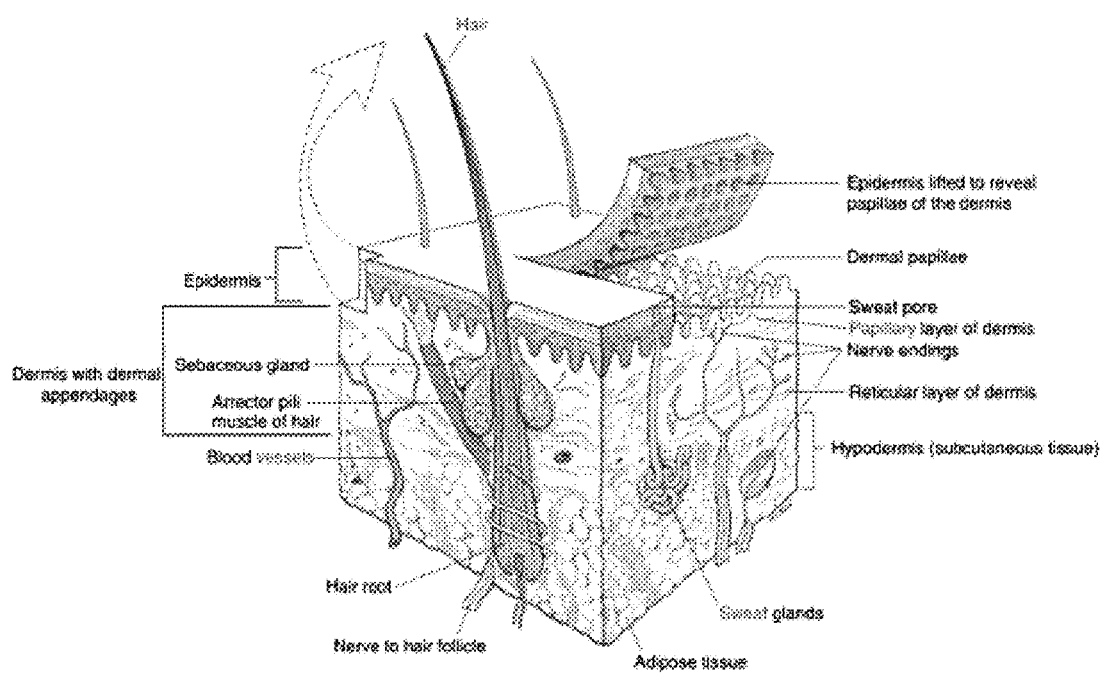
FIG. 1 presents a diagram of skin anatomy. Taken from Stedman's Medical Dictionary, 27th Ed., Lippincott, Williams & Wilkins, Baltimore, Md. (2000), at 1647.
Figure 2:
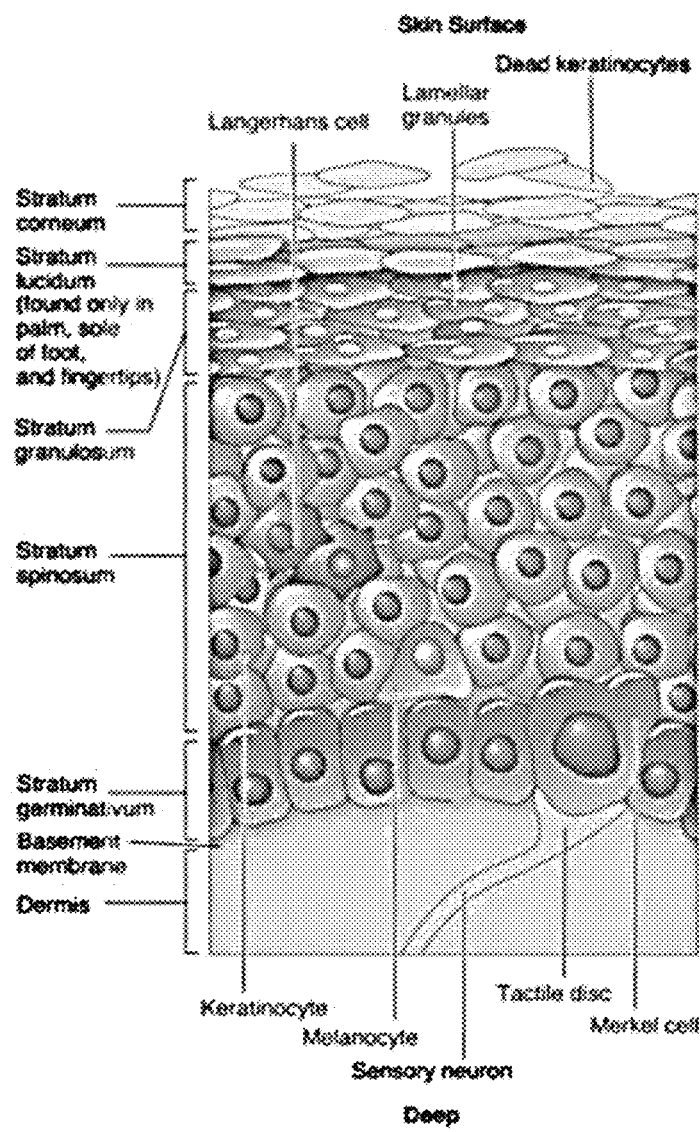
FIG. 2 depicts layers of the epidermis.

The term "active therapeutic agent" as used herein refers to a drug, molecule, nucleic acid, protein, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably.

The term "administer" as used herein means to give or to apply. The term "administering" as used herein includes in vivo administration, as well as administration directly to tissue ex vivo.

The term "alginate" as used herein is an anionic biopolymers produced by a variety of microorganisms and marine algae. Alginate is a polysaccharide that comprises β-D-mannuronic acid units and α-L-guluronic acid units. Some alginate polymers are block copolymers with blocks of the guluronic acid (or salt) units alternating with blocks of the mannuronic acid (or salt) units. Some alginate molecules have single units of guluronic acid (or salt) alternating with single units of mannuronic acid (or salt). The ratio and distribution of the mannuronic and guluronic unit, along with the average molecular weight, affect the physical and chemical properties of the copolymer. See Haug, A. et al., Acta Chem. Scand., 183-90 (1966). Alginate polymers have viscoelastic rheological properties and other properties that make it suitable for some medical applications. See Klock, G. et al., "Biocompatibility of mannuronic acid-rich alginates," Biomaterials, Vol. 18, No. 10, 707-13 (1997).

The term "analgesic" as used herein refers to any member of a group of drugs used to provide relief from pain. "Analgesic agents" act in various ways on the peripheral and central nervous systems, and are distinct from "anesthetic agents.

The term "analog" as used herein refers to a compound having a structure similar to another, but differing from it, for example, in one or more atoms, functional groups, or substructure.

The term "anesthetic agent" as used herein refers to an agent that reversibly produces a reduction or loss of sensation.

The term "anionic lipid" as used herein refers to a lipid which has a negative charge. Exemplary anionic lipids include, without limitation, diacylglycerolhemisuccinates, e.g. DOGS, DMGS, POGS, DPGS, DSGS; diacylglycerol-hemimalonates, e.g. DOGM or DMGM; diacylglycerol-hemiglutarates, e.g. DOGG, DMGG; diacylglycerolhemi-adipates, e.g. DOGA, DMGA; diacylglycerolhemicyclohexane-1, 4-dicarboxylic acids, e.g. DO-cHA, DM-cHA; (2, 3-Diacyl-propyl) amino}-oxoal-kanoic acids e.g. DOAS, DOAM, DOAG, DOAA, DMAS, DMAM, DMAG, DMAA; Diacyl-alkanoic acids, e.g. DOP, DOB, DOS, DOM, DOG, DOA, DMP, DOB, DMS, DMM, DMG, DMA; Chemicals and derivatives thereof, e.g. Chol-C2, Chol-C3, Chol-05, Chol-C6, Chol-C7 or Chol-C8; Chol-CI, CholC3N or Cholesterolhemidicarboxylic acids and Cholesteryloxycarbonylaminocarboxylic acids, e.g. Chol-C12 or CholC13N, fatty acids, e.g. Oleic acid, Myristic Acid, Palmitic acid, Stearic acid, Nervonic Acid, Behenic Acid; DOPA, DMPA, DPPA, POPA, DSPA, Chol-S04, DOPG, DMPG, DPPG, POPG, DSPG or DOPS, DMPS, DPPS, POPS, DSPS or Cetyl-phosphate.

The aforementioned lipids may be formed with or without cholesterol, or with a derivative of cholesterol (e.g., cholesterol sulfate).

The terms "anti-neoplastic agent", "anticancer agent" or "chemotherapeutic agent" are used interchangeably to refer to an agent that inhibits growth, proliferation, and spread of a neoplasm. Non-limiting examples of anti-neoplastic agents include 5-fluorouracil, adriamycin, daunorubicin, cytarabine, vincristine, actinomycin D, mitomycin, bleomycin, acrarubicin, and combinations thereof. According to some embodiments, the anti-neoplastic agent can be entrapped in a lysosome. For the antineoplastic agent to be entrapped in the liposomes according to the invention, any such agent can be selected, provided the agent does not inhibit liposome formation.

The term "antihistamine agent" as used herein refers to any of various compounds that counteract histamine in the body and that are used for treating allergic reactions (such as hay fever) and cold symptoms. Non-limiting examples of antihistamines usable in context of the described invention include chlorpheniramine, brompheniramine, dexchlorpheniramine, tripolidine, clemastine, diphenhydramine, promethazine, piperazines, piperidines, astemizole, loratadine and terfenadine.

As used herein the term "anti-inflammatory agent" refers to a therapeutic agent that counteracts and inhibits the process of inflammation and swelling. The term "non-steroidal anti-inflammatory agent" as used herein refers to a large group of agents that are aspirin-like in their action, including, but not limited to, ibuprofen (Advil®), naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. One example is etofenamate, a flufenamic acid derivative.

The term "anti-oxidant agent" as used herein refers to a substance that inhibits oxidation or reactions promoted by oxygen or peroxides. Non-limiting examples of anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5, 7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

The term "anti-static" refers to a compound used to treat materials or their surfaces in order to reduce or eliminate buildup of static electricity.

The term "apply" as used herein refers to placing in contact with or to lay or spread on.

The term "arabinogalactan" as used herein refers to a wood sugar extracted from the Western Larch tree (also known as larch gum). Arabinogalactans are complex, highly branched polymers of arabinose and galactose in the ratio of from about 1:3 to about 1:10, i.e., 1:3, 1:4, 1:5, 1:6, 1:7, 1:8, 1:9 or 1:10. A commercially available example is Laracare®200 from Lonza, Inc.

The term "bactericide" as used herein refers to a substance that kills bacteria. Bactericides may be disinfectants, antiseptics, antibiotics, etc.

The term "bio-distribution" as used herein refers to a method of tracking where drugs, active therapeutic agents, compounds of interest etc. travel in the subject in need thereof.

The term "buffer" refers to an aqueous solution consisting of a mixture of a weak acid and its conjugate base, or vice versa. The pH changes very little when a small or moderate amount of strong acid or base is added to it, and thus it is used to prevent changes in the pH of a solution.

The term "carrier" as used herein describes a material that does not cause significant irritation to an organism and does not abrogate the biological activity and properties of the compound of the composition of the described invention. Carriers must be of sufficiently high purity and of sufficiently low toxicity to render them suitable for administration to the mammal being treated. The carrier can be inert, or it can possess pharmaceutical benefits. The terms "excipient", "carrier", or "vehicle" are used interchangeably to refer to carrier materials suitable for formulation and administration of pharmaceutically acceptable compositions described herein.

The term "cationic lipid" as used herein refers to a lipid which has a positive charge. Exemplary cationic lipids include, without limitation, DOTAP, DMTAP, DPTAP, DSTAP, POTAP, DODAP, PODAP, DMDAP, DPDAP, DSDAP, DODMHEAP or DORI, PODMHEAP or PORI, DMDMHEAP or DMRI, DPDMHEAP or DPRI, DSDMHEAP or DSRI, DOMDHEAP, POMDHEAP, DMMDHEAP, DPMDHEAP, DSMDHEAP, DOMHEAP, POMHEAP, DMMHEAP, DPMHEAP, DSMHEAP, DODHEAP, PODHEAP, DMDHEAP, DPDHEAP, DSDHEAP, DDAB, DODAC, DOEPC, DMEPC, DPEPC, DSEPC, POEPC, DORIE, DMRIE, DOMCAP, DOMGME, DOPSP, DOP6P, DC-Choi, TC-Chol, DAC-Chol, Chol-Betaine, N-methyl-PipChol, CTAB, DOTMA, MoChol, HisChol, Chim, MoC3Chol, Choi-C3N-Mo3, Chol-C3N-Mo2, Choi-C4N-Mo2, Chol-DMC3N-Mo2, CholC4Hex-Mo2, DmC4Mo2, DmC3Mo2, C3Mo2, C3Mo3, C5Mo2, C6Mo2, C8Mo2, C4Mo4, PipC2-Chol, MoC2Chol, PyrroC2Chol, ImC3Chol, PyC2Chol, MoDO, MoDP, DOIM or DPIM.

The term "chemical driver" as used herein refers to a component or components of the formulation of the described invention that provides the driving force for a drug to diffuse from the vehicle, into and through the stratum corneum of the skin. According to some embodiments, the chemical drivers of the described invention synergistically cooperate to deliver the therapeutic agent.

The term "cholesterol" as used herein refers to a monohydric secondary alcohol of the cyclopentenophenantrene (4-ring fused) system containing one double bond. According to some embodiments, cholesterol is a liposome component. According to some embodiments, it is useful to enhance incorporation and emulsification of medicinal products in oils or fats.

The term "colorant" as used herein refers to a substance used to impart a color on a composition to improve the attractiveness of the composition and/or to enable easy product identification. Non-limiting examples of colorants include oil-soluble dyes, oil dispersible dyes, water-soluble dyes, e.g. acid blue 3, acid blue 104, acid green 1, acid green 25, acid yellow 3, acid yellow 73 sodium salt, D&C green No. 5, 6, & 8, D&C yellow No. 7, 8, 10, & 11, D&C violet No. 2, FD&C blue No. 1 & 2, FD&C green No. 3, FD&C yellow No. 5 & 6, and mixtures thereof.

The term "compatible" as used herein refers to a property of components of a composition whereby the components are capable of being combined with each other in a manner such that there is no interaction that would substantially reduce the efficacy of the composition under ordinary use conditions.

The term "component" as used herein refers to a constituent part, element or ingredient.

The terms "composition" and "formulation" are used interchangeably herein to refer to a product of the described invention that comprises all active and inert ingredients.

The term "condition" as used herein, refers to a variety of health states and is meant to include disorders or diseases caused by any underlying mechanism or disorder, injury, and the promotion of healthy tissues and organs.

The term "consequence" as used herein refers to an effect, result or outcome of something that occurred earlier.

The term "contact" and all its grammatical forms as used herein refers to a state or condition of touching or of immediate or local proximity.

The term "controlled release" as used herein refers to a drug-containing formulation in which the manner and profile of drug release from the formulation are controlled. This includes immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that may result in substantially constant levels of a drug over an extended time period. The term "delayed release" is used herein in its conventional sense to refer to a drug formulation in which there is a time delay between administration of the formulation and the release of the drug therefrom. "Delayed release" may or may not involve gradual release of drug over an extended period of time, and thus may or may not be "sustained release." The term "long-term" release, as used herein, means that the drug formulation is constructed and arranged to deliver therapeutic levels of the active ingredient for at least: 2 hours, 3 hours, 4 hours, hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 73 hours, 74 hours, 75 hours, 76 hours, 77 hours, 78 hours, 79 hours, 80 hours, 81 hours, 82 hours, 83 hours, 84 hours, 85 hours, 86 hours, 87 hours, 88 hours, 89 hours, 90 hours, 91 hours, 92 hours, 93 hours, 94 hours, 95 hours, 96 hours, 97 hours, 98 hours, 99 hours, 100 hours, 101 hours, 102 hours, 103 hours, 104 hours, 105 hours, 106 hours, 107 hours, 108 hours, 109 hours, 110 hours, 111 hours, 112 hours, 113 hours, 114 hours, 115 hours, 116 hours, 117 hours, 118 hours, 119 hours, or 120 hours.

The term "copolymer" as used herein refers to a polymer derived from more than one species of monomer. The term "polymer" refers to a large molecule, or macromolecule, composed of many repeated subunits. The term "monomer" refers to a molecule that may bind chemically to other molecules to form a polymer.

The term "derivative" as used herein means a compound that may be produced from another compound of similar structure in one or more steps. A derivative of a compound retains at least a degree of the desired function of the compound. Accordingly, an alternate term for "derivative" may be "functional derivative." Derivatives can include chemical modifications, such as alkylation, acylation, carbamylation, iodination or any modification that derivatizes the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. See, e.g., Methods and Analytical Procedures, Elsevier Biomedical Press, New York (1975).

The term "disease" or "disorder" as used herein refers to an impairment of health or a condition of abnormal functioning.

The term "drug" as used herein refers to a substance intended for use in the diagnosis, cure, mitigation, treatment or prevention of disease or disorder, or to affect the structure or function of the body.

The terms "effective therapeutic amount", an "amount effective", or "pharmaceutically effective amount" of one or more of the active agents is used interchangeably to refer to an amount that is sufficient to provide the intended benefit of treatment. An effective amount of an active agent that can be employed according to the described invention generally ranges from about 0.01 mg/kg body weight to about 100 g/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

The terms "emollient" or "moisturizer" as used herein are used interchangeably to refer to complex mixtures of chemical agents specially designed to make the external layers of the skin (epidermis) softer and more pliable. An emollient increases the skin's hydration (water content) by reducing evaporation.

The term "emulsifier" as used herein refers to an additive that help two liquids mix. For example, water and oil separate in a glass, but adding an emulsifier will help the water and oil to mix together.

The term "excipient" as used herein refers to any inactive ingredient that is added to the composition of the described invention and that is not intended to exert therapeutic effects at the intended dosage, although it may act to improve product delivery. Additional characteristics of excipients can be found in the Guidance for Industry Nonclinical Studies for the Safety Evaluation of Pharmaceutical Excipients issued by the US Food and Drug Administration Center for Drug Evaluation and Research (May, 2005), herein incorporated by reference.

The term "flocculant" as used herein refers to a substance that promotes the clumping of particles.

The term "fragrant" as used herein refers to an aroma compound, also known as odorant, or flavorant, which is a chemical compound that has a smell or odor r when it is sufficiently volatile to be transported to the olfactory system in the upper part of the nose. Generally molecules meeting this specification will have molecular weights of <300 g/mole. Flavors affect both the sense of taste and smell, whereas fragrances affect only smell. Generally, flavors tend to be naturally occurring, while fragrances tend to be synthetic. Aroma compounds can be found in food, wine, spices, perfumes, fragrance oils, and essential oils.

The term "hydrogel' as used herein refers to a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content.

The term "hydrophilic" as used herein refers to a material or substance having an affinity for polar substances, such as water.

The term "impregnate" as used herein in its various grammatical forms refers to causing to be infused or permeated throughout, or to fill interstices with a substance.

As used herein the term "inflammation" refers to a physiologic response to infection and injury in which cells involved in detoxification and repair are mobilized to the compromised site by inflammatory mediators. The term "acute inflammation" as used herein, refers to inflammation, usually of sudden onset, characterized by the classical signs, with predominance of the vascular and exudative processes. The term "chronic inflammation" as used herein refers to inflammation of slow progress and marked chiefly by the formation of new connective tissue; it may be a continuation of an acute form or a prolonged low-grade form, and usually causes permanent tissue damage.

The term "lipid" as used herein refers to a group of naturally occurring molecules that include fats, waxes, sterols, fat-soluble vitamins (e.g. vitamins A, D, E, and K), mono-di or triglycerides phospholipids, and others. The main biological functions of lipids include storing energy, signaling, and acting as structural components of cell membranes. Exemplary lipids include natural phospholipids (e.g., egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanol amine, diphosphatidyl glycerol, cardiolipin and plasmalogen); synthetic lipids (e.g., dicetyl phosphate, distearoyl phosphatidyl choline, dioleoylphosphatidyl ethanol amine, dipalmitoyl phosphatidyl choline, diphalmitoyl phosphatidyl ethanol amine, diphalmitoyl phosphatidyl serine, eleostearoyl phosphatidyl choline, eleostearoyl phosphatidyl ethanol amine and eleostearoyl phosphatidyl serine); hydrogenated products that may be obtained from the natural phospholipids or synthetic lipids; derivatives of the natural phospholipids or synthetic lipids; and fatty acid mixtures that may be obtained by hydrolysis of the natural phospholipids or synthetic lipids.

The term "lipophilic" as used herein refers to preferring or possessing an affinity for a non-polar environment compared to a polar or aqueous environment.

The term "liposome" as used herein refers to a man-made spherical vesicle containing at least one lipid bilayer. The liposome can be used as a vehicle for administration of components, such as, but not limited to, pharmaceutical compositions and pharmaceutical formulations, active therapeutic agents, drugs, enzymes, other proteins and peptides, and DNA and RNA fragments, etc.

The terms "local anesthetic" or "analgesic agents" are used interchangeably herein to refer to any drug that provides local numbness or moderation of painful signals that although still perceived are no longer painful, or any drug that provides a regional blockage of nociceptive pathways (afferent and/or efferent). "Local anesthetic" as used herein also encompasses drugs not traditionally associated with local anesthetic properties but which have a local anesthetic effect, for example, non-narcotic analgesics, such as, acetylsalicylic acid, ketoprofen, piroxicam, diclofenac, indomethacin, ketorolac, rofecoxib, and celecoxib, and pharmaceutically acceptable salts thereof, or mixtures thereof.

The phrase "localized administration", as used herein, refers to administration of a therapeutic agent in a particular location in the body.

The phrase "localized pharmacologic effect", as used herein, refers to a consequence of treatment or a therapeutic effect limited to a certain location, i.e. in proximity to a certain location, place, area or site. The phrase "predominantly localized pharmacologic effect", as used herein, refers to a therapeutic effect of a drug that is limited to a certain location by at least 1 to 3 orders of magnitude, which is achieved by a localized administration as compared to a systemic administration.

The term "lubricant" as used herein refers to a substance introduced to reduce friction between surfaces in mutual contact, which ultimately reduces the heat generated when the surfaces move. It may also have the function of transmitting forces, transporting foreign particles, or heating or cooling the surfaces.

The term "matrix" as used herein refers to a three dimensional network of fibers that contains voids (or "pores") where the fibers intersect. The structural parameters of the pores, including the pore size, porosity, pore interconnectivity/tortuosity and surface area, affect how substances (e.g., fluid, solutes) move in and out of the matrix.

The term "maximum tolerated dose" as used herein refers to the highest dose of a drug that does not produce unacceptable toxicity.

The terms "minimum effective concentration," "minimum effective dose," or "MEC" are used interchangeably to refer to the lowest concentration of a drug required to produce a desired pharmacological effect in most patients.

The terms "neoplasm" or "tumor" as used herein are used interchangeably to refer to an abnormal mass of tissue that results when cells divide more than they should or do not die when they should. Neoplasms may be benign (not cancer) or malignant (cancer). For example, a benign neoplasm (or benign tumor) is a tumor that stops growing by itself, does not invade other tissues and does not form metastases The term "neutral lipid" as used herein refers to a lipid which has neither a positive or negative charge. Exemplary neutral lipids include, without limitation, cholesterol, cholesterol esters, triglycerides and fatty acids.

The term "non-cellulosic copolymer" as used herein refers to a copolymer not containing or derived from cellulose. The term "cellulose" as used herein refers to a natural carbohydrate high polymer (polysaccharide) consisting of anhydroglucose units joined by an oxygen linkage to form long molecular chains that are essentially linear that can be hydrolyzed to glucose.

The term "pain" as used herein refers to a distressing feeling often caused by intense or damaging stimuli. As such, the term "pain" is characterized by an unpleasant sensory detected and signaled by the nerves and emotional experience associated with actual or potential tissue damage.

The terms "penetration enhancer" and "permeation enhancer" are used interchangeably to refer to natural or synthetic molecules that facilitate the transport of co-administered active agents across biological membranes.

The term "pharmaceutical composition" is used herein to refer to a composition that is employed to prevent, reduce in intensity, cure or otherwise treat a target condition or disease.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

As used herein the phrase "pharmaceutically acceptable carrier" refers to any substantially non-toxic carrier useable for formulation and administration of the composition of the described invention in which the product of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmacologic effect", as used herein, refers to a result or consequence of exposure to an active agent.

The term "pharmacokinetics" as used herein describes how the body affects a specific drug after administration through the mechanisms of absorption and distribution, as well as the chemical changes of the substance in the body (e.g. by metabolic enzymes such as cytochrome P450 or glucuronosyltransferase enzymes), and the effects and routes of excretion of the metabolites of the drug.

The term "plasticizer" as used herein refers to an additive that increases the plasticity or fluidity of a material.

The term, "polyethylene glycol" as used herein is used to refer to a condensation polymer of ethylene glycol with the general formula $HOCH_2(CH_2OCH_2)nCH_2OH$ or $H(OCH_2CH_2)_nOH$. Average molecular weights range from 200 to 6000. Polyethylene glycols can be used as medicaments for topical application in the treatment of wounds, for the treatment of inflammatory skin disease, for the prevention of scar formation and/or for enhancing the repair of damaged skin or mucosa.

The term "polymer" as used herein refers to a molecule formed by the chemical union of two or more monomer or oligomer units. The chemical units are normally linked together by covalent linkages. The two or more combining units in a polymer can be all the same, in which case the polymer is referred to as a homopolymer. They can also be different and, thus, the polymer will be a combination of the different units. Such polymers are referred to as copolymers. The relationship between the polymer subunits may be oriented head-to-head or head-to-tail relative to each subunit. Polymers can be divided into two broad groups: synthetic (non-natural polymers) and natural polymers.

Examples of non-natural polymers include, but are not limited to polyalcohols such as ethylene vinyl alcohol (EVAL), hydroxyethyl acrylate, poly(ethylene glycol), poly (vinyl alcohol), poly(hydroxypropyl methacrylamide), poly (propylene glycol); polyamines (such as polyvinylamine, polyallylamine, tetramethyleneamine, pentamethyleneamine, hexamethyleneamine, bis(2-hydroxyethyl)amine, bis(2-aminoethyl)amine, tris(2-aminoethyl)amine, branched or linear polyethyleneimine e.g., Lubrasols™- and salts thereof, and derivatives of polyethyleneimine such as acylated polyethyleneimine); dendrimers (such as polyamidoamine (PAMAM) Starburst dendrimers); polyalkylene glycol derivatives (such as amine-substituted polyethylene and polypropylene glycols); polyacrylates (such as amine-substituted and alcohol-substituted polyacrylates); multi-amino PEG; polymers where the backbone polymeric structure is substituted with the following pendant nucleophilic or electrophilic groups such as PEG substituted with amines, hydroxylamine, hydrazines, thiols, xanthates, amides, hydrazides, sulfonamides, oximes, malonates, imides, aldehydes, succinim idyl, isocyanates, vinylsulfones, oxiranes, arylhalides, allylhalides, alkyl halides, esters, ethers or anhydrides.

Examples of anionic biopolymers include carboxymethylcellulose and salts thereof, salts of carboxymethyl and carboxymethylhydroxyethyl starches, and other glucoaminoglycans such as chondroitin sulfate, dermatan sulfate, heparin and heparin sulfate and keratin sulfates.

Examples of natural polymers include, without limitation, hyaluronic acid, chondroitin sulfate, alginate, guar gum, fructan, arabinogalactan and any corresponding salt or derivative of thereof.

Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from other glycosaminoglycans in that is free from covalent links to protein and sulphonic groups. Hyaluronic acid is ubiquitous in animals, with the highest concentration found in soft connective tissue. The viscoelastic properties of hyaluronic acid, that is, hard elastic under static conditions though less viscous under small shear forces, enables hyaluronic acid to basically function as a shock absorber for cells and tissues. Hyaluronic acid also has a relatively large capacity to absorb and hold water. These properties of hyaluronic acid are dependent on the molecular weight, the solution concentration, and physiological pH. At low concentrations, the individual chains entangle and form a continuous network in solution, which gives the system pronounced viscoelasticity and pseudoplasticity that is unique for a water-soluble polymer at low concentration.

As used herein, the term "fructan" refers to all oligosaccharides and polysaccharides that have a majority of anhydro fructose units and derivatives thereof. The fructan can have a polydisperse chain length distribution and can be straight-chain or branched. The fructans include primarily β-2,6 bonds as in levan, or β-2,1 bonds as in a carboxyl modified fructant, e.g., inulin.

Examples of synthetic polymers include, without limitation, polyethylene, polystyrene, polyester, polyvinyl chloride, polyamide, polypropylene, and nylon.

The term "polymersome" as used herein refers to a class of artificial vesicles, tiny hollow spheres that enclose a solution. Polymersomes are made using amphiphilic synthetic block copolymers to form the vesicle membrane, and have radii ranging from 50 nm to 5 μm or more. Most reported polymersomes contain an aqueous solution in their core and are useful for encapsulating and protecting sensitive molecules, such as but not limited to pharmaceutical compositions and pharmaceutical formulations, active therapeutic agents, drugs, enzymes, other proteins and peptides, and DNA and RNA fragments, etc. The polymersome membrane provides a physical barrier that isolates the encapsulated material from external materials, such as those found in biological systems.

The term "potency" as used herein refers to efficacy, effectiveness, or strength of a drug. The potency of a drug is the reciprocal of dose, and has the units of persons/unit weight of drug or body weight/unit weight of drug. Relative potency compares the relative activity of drugs in a series relative to some prototypic member of the series. "Efficacy" connotes the property of a drug to achieve the desired response, and maximum efficacy denotes the maximum achievable effect.

The terms "povidone" "2-pyrrolidinone", "polyvinylpyrrolidone" and PVP are used interchangeably to refer to a synthetic polymer consisting of linear 1-vinyl-2-pyrrolidinone groups. PVP is produced commercially as a series of products having mean molecular weights ranging from about 10,000 to about 700,000. The viscosity of solutions containing 10% or less PVP is essentially the same as that of water; solutions more concentrated than 10% become more viscous, depending on the concentration and molecular weight of the polymer used.

The term "preservative" as used herein refers to a substance that is added to a product to prevent decomposition by microbial growth or by undesirable chemical changes.

The term "reduced" or "to reduce" as used herein refers to a diminution, a decrease, an attenuation or abatement of the degree, intensity, extent, size, amount, density or number.

The term "release" as used herein and its various grammatical forms, refers to dissolution of an active drug component and diffusion of the dissolved or solubilized species. According to some embodiments, this occurs by a combination of the following processes: (1) hydration of a matrix, (2) diffusion of a solution into the matrix; (3) dissolution of the drug; and (4) diffusion of the dissolved drug out of the matrix.

The term "similar" is used interchangeably with the terms analogous, comparable, or resembling, meaning having traits or characteristics in common.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent. A "suspension" is a dispersion (mixture) in which a finely-divided species is combined with another species, with the former being so finely divided and mixed that it doesn't rapidly settle out. In everyday life, the most common suspensions are those of solids in liquid.

The terms "solubility enhancer" or "solubilizing agent" are used interchangeably to refer to any chemical and/or biological agent able to improve the solubility of an agent in a solvent. Exemplary solubility enhancers include povidone, cholesterol, cyclodextrins, and polyethylene glycols. Exemplary solubility enhancers also include surfactants, which act as solubilizing agents by forming micelles. The HLB system is used to describe the characteristics of a surfactant. It is an arbitrary scale to which HLB values are experimentally determined and assigned. If the HLB value is low, the number of hydrophilic groups on the surfactant is small, which means it is more lipophilic (oil soluble) than hydrophilic (water soluble). Conversely, if the HLB value is high, there are a large number of hydrophilic groups on the surfactant, which makes it more hydrophilic (water soluble) than oil soluble. An HLB value of 10 or higher means that the agent is primarily hydrophilic.

The term "solvent" as used herein refers to a substance capable of dissolving another substance (termed a "solute") to form a uniformly dispersed mixture (solution).

The term "stabilizer" as used herein refers to a chemical which tends to inhibit the reaction between two or more other chemicals, for example, thymol.

As used herein the term "steroidal anti-inflammatory agent", refers to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The terms "subject" or "individual" or "patient" are used interchangeably to refer to a member of an animal species of mammalian origin an animal species of mammalian origin, including but not limited to, mouse, rat, cat, goat, sheep, horse, hamster, ferret, pig, dog, platypus, guinea pig, rabbit and a primate, such as, for example, a monkey, ape, or human.

The phrase "subject in need thereof" as used herein refers to a subject that (i) will be administered a topical composition of the described invention; (ii) is applying the topical composition of the described invention; or (iii) has applied the topical composition of the described invention, unless the context and usage of the phrase indicates otherwise.

When using the terms "substantial", "substantially", "essential" or "essentially" herein it is intended that the feature which is described by these terms is present in an amount or has an impact which provides for a technical effect with relevance for the exercise of the presently claimed invention. For instance, a "substantial amount" of a substance in a composition is an amount which provides for a technical effect exhibited by the substance to a degree which provides for a technical effect in terms of the described invention. Likewise, if a composition is indicated as comprising "substantially no" with respect to a substance, this means that the composition is allowed to include insignificant amounts of the substance, as long as these amounts do not have any technical impact on the other ingredients in the composition and does not in itself "make a difference" or put in other words, "substantially no" and "essentially no" means that e.g. trace amounts or effects may be present as long as they do not have an overall technical influence.

The term "surfactant" as used herein refers to a compound that lowers the surface tension (or interfacial tension) between two liquids or between a liquid and a solid.

The term "susceptible" as used herein refers to being at risk for.

The term "synergistic effect" as used herein, refers to a combined effect of two chemicals, which is greater than the sum of the effect of each agent given alone.

The phrase "systemic administration", as used herein, refers to administration of a therapeutic agent with a pharmacologic effect on the entire body. Systemic administration includes enteral administration (e.g. oral) through the gastrointestinal tract and parenteral administration (e.g. intravenous, intramuscular, etc.) outside the gastrointestinal tract.

The terms "therapeutic amount", "therapeutic effective amount" or an "amount effective" of one or more of the therapeutic agents is an amount that is sufficient to provide the intended benefit of treatment. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. Generally, a maximum dose should be used, that is, the highest safe dose according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein. Additionally, the terms "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. Topical administration, in contrast to transdermal administration, generally provides a local rather than a systemic effect.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "thickening agent" refers to a substance that can increase the viscosity of a liquid without substantially changing its other properties.

The term "thinning agent" as used herein refers to a substance that reduces the viscosity of a liquid making it easier to apply.

The term "topical" refers to administration of a pharmaceutical composition at, or immediately beneath, the point of application. The terms "topically", "topical administration" and "topically applying" are used interchangeably to refer to delivering a pharmaceutical composition of the described invention onto one or more surfaces of a tissue or cell, including epithelial surfaces. The composition may be applied by pouring, dropping, or spraying, if a liquid; rubbing on, if an ointment, lotion, cream, gel, or the like; dusting, if a powder; spraying, if a liquid or aerosol composition; or by any other appropriate means. Topical administration generally provides a local rather than a systemic effect.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

As used herein the term "vasoconstrictor" is used to describe an active therapeutic agent that causes a narrowing of blood vessels resulting from contraction of the muscular wall of the vessels, in particular the large arteries and small arterioles. The process is the opposite of vasodilation, the widening of blood vessels.

The term "vitamin" as used herein, refers to any of various organic substances essential in minute quantities to the nutrition of most animals act especially as coenzymes and precursors of coenzymes in the regulation of metabolic processes.

The term "wetting agent" as used herein refers to a substance that reduces the surface tension of water in order to allow it to spread drops onto a surface, thereby increasing the spreading abilities of a liquid.

The term "wound healing agent" as used herein refers to an agent that promotes an intricate process where the skin or other body tissue repairs itself after injury. In normal skin, the epidermis (surface layer) and dermis (deeper layer) form a protective barrier against the external environment. As such, the term "wound healing agent" refers to any substance that facilitates the wound healing process.

The term "zwitterion" is a neutral molecule with a positive and a negative electrical charge.

According to one aspect, the described invention provides a topical delivery system comprising a pharmaceutical composition formulated for application directly to a skin of a subject in need thereof comprising (a) a therapeutic amount of an active therapeutic agent that is effective to treat symptoms of a disease, disorder or condition; (b) a chemical driver comprising an amino benzoate local anesthetic, ethoxydiglycol and methylsulfonylmethane (MSM), wherein the chemical drivers are effective to deliver the therapeutic agent to the skin; and (c) a depot component that is effective to keep the active agent locally in the skin and to reduce distribution of the active to the blood stream.

Depot Components for Keeping the Pharmaceutical Formulation in the Skin and Facilitating Controlled Release of the Active Agent According to some embodiments, the composition of the described invention contains a depot component that is effective for keeping the active agent concentrated locally in the skin. According to some such embodiments, the depot component is effective to facilitate controlled or delayed type release of the active therapeutic agent. According to some embodiments, the depot component reduces the potential of the active agent, active metabolite, the chemical drivers, or a combination thereof to enter the bloodstream. According to some embodiments, the chemical driver component that remains in the skin is effective to allow the active agent and/or the active metabolite to further diffuse away from the skin, such that the active agent can execute its biological function at the specific tissue of interest. According to some embodiments, the depot component comprises a liposome. According to some embodiments, the depot component comprises a polymer. According to some embodiments, the depot component comprises a complex of a liposome and a polymer or a polymersome. Other examples of depot components include, without limitation, micelles, reverse micelles, emulsions, microemulsions, etc.

Liposomes are generally known as sub-micron spherical vesicles comprised of phospholipids and cholesterol that form a hydrophobic bilayer surrounding an aqueous core. These structures have been used with a wide variety of therapeutic agents and allow for a drug to be entrapped within the liposome based in part upon its own hydrophobic (e.g. bilayer entrapment) or hydrophilic properties (e.g. entrapment in the aqueous compartment). Liposomes are generally used for controlled release and for drug targeting of lipid-capsulated compounds (Betageri et al, Liposome Drug Delivery Systems, Technomic Publishing Co., Inc., Lancaster, Pa., 1993).

Typically, encapsulating a drug, an active therapeutic agent or a pharmaceutical composition in a liposome can alter the pattern of bio-distribution and the pharmacokinetics for the drugs. In certain cases, liposomal encapsulation has been found to lower drug toxicity. For example, long circulating liposomal formulations can avoid uptake by organs of the mononuclear phagocyte system, primarily in the liver and spleen. According to some embodiments, such long-circulating liposomes may include a surface coat of flexible water soluble polymer chains that act to prevent interaction between the liposome and plasma components that play a role in liposome uptake. According to some embodiments, such liposomes can be made of saturated, long-chain phospholipids and cholesterol, without this coating.

Exemplary liposomes may comprise a lipid layer comprising liposome forming lipids. The lipid may include at least one phosphatidyl choline which provides the primary packing/entrapment/structural element of the liposome. The phosphatidyl choline comprises mainly $C_{16}$ or longer fatty-acid chains. Chain length provides for both liposomal structure, integrity, and stability. Optionally, one of the fatty-acid chains may have at least one double bond. As used herein, the term "phosphatidyl choline" includes, without limitation, soy PC, egg PC dielaidoyl phosphatidyl choline (DEPC), lecithin, dioleoyl phosphatidyl choline (DOPC), distearoyl phosphatidyl choline (DSPC), hydrogenated soybean phosphatidyl choline (HSPC), dipalmitoyl phosphatidyl choline (DPPC), 1-palmitoyl-2-oleo phosphatidyl choline (POPC), dibehenoyl phosphatidyl choline 30 (DBPC), and dimyristoyl phosphatidyl choline (DMPC).

As used herein, the term "Soy-PC" refers to phosphatidyl choline compositions including a variety of mono-, di-, tri-unsaturated, and saturated fatty acids. Soy-PC may include palmitic acid present in an amount of about 12% to about 33% (i.e., about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, or about 33%) by weight; stearic acid present in an amount of about 3% to about 8% (i.e., about 3%, about 4%, about 5%, about 6%, about 7%, or about 8%) by weight; oleic acid present in an amount of about 4% to about 22% (i.e., about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, or about 22%), by weight; linoleic acid present in an amount of about 60% to about 66% (i.e., about 60%, about 61%, about 62%, about 63%, about 64%, about 65%, or about 66%) by weight; and linolenic acid present in an amount of about 5% to about 8% (i.e., about 5%, about 6%, about 7%, or about 8%) by weight.

As used herein, the term "Egg-PC" refers to a phosphatidyl choline composition including, but not limited to, a variety of saturated and unsaturated fatty acids. For example, Egg-PC may comprise palmitic acid present in an amount of 10 about 34% (i.e., about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33% or 3 about 4%) by weight; stearic acid present in an amount of about 10% by weight; oleic acid present in an amount of about 31% by weight; and linoleic acid present in an amount of about 18% by weight.

According to some embodiments, the liposome comprises cholesterol. The ratio of phosphatidyl choline to cholesterol may be, for example, from about 0.5:1 to about 4:1 by mole ratio. According to some embodiments, the ratio of phosphatidyl choline to cholesterol may be from about 1:1 to about 2:1 by mole ratio, e.g., about 1.1; about 1.1:1; about 1.2:1: about 1.3:1; about 1.4:1; about 1.5:1; about 1.6:1; about 1.7:1; about 1.8:1; about 1.9:1, or about 2:1. According to some embodiments, the ratio of phosphatidyl choline to cholesterol may be about 2:1 by mole ratio.

As used herein the term "total lipid" includes phosphatidyl cholines and any anionic phospholipid present in the liposome membrane.

The liposome may also comprise physiologically acceptable salts to maintain proper isotonicity. Any pharmaceutically acceptable salt that achieves isotonicity is acceptable, including, without limitation, for example, e.g. NaCl.

The liposomes of the described invention may comprise a lipid layer of phospholipids and cholesterol. According to some embodiments, the ratio of phospholipid to cholesterol is sufficient to form a liposome that will not dissolve or disintegrate once administered to the animal. The phospholipids and cholesterol may be dissolved in suitable solvent or solvent mixtures. After a suitable amount of time, the solvent is removed via vacuum drying and/or spray drying. The resulting solid material can be stored or used immediately. Subsequently, the resulting solid material is hydrated in an aqueous solution containing an appropriate concentration of the therapeutic agent at an appropriate temperature, resulting in multilamellar vesicles (MLV). The solutions containing MLV can be size-reduced via homogenization to form Small Unilameller Vesicles (SUVs) with the drug passively entrapped within the formed SUVs. The resulting liposome solution can be separated from unencapsulated therapeutic agent, for example by chromatography or filtration, and then filtered for use.

According to some embodiments, an anionic liposome may also be used. According to some embodiments, an anionic liposome provides a Coulombic character to the liposomes. According to some embodiments, anionic lipids can help stabilize the system upon storage, can prevent fusion or aggregation or flocculation, and can facilitate or enable freeze drying. Exemplary anionic lipids include, without limitation, phospholipids in the phosphatidic acid, phosphatidylglycerol, and phosphatidylserine classes (PA, PG, and PS). Further examples include C16 or larger fatty-acid chains. Further exemplary anionic phospholipid include, without limitation, Egg-PG (Egg Phosphatidylglycerol), Soy-PG (Soy-Phosphatidylglycerol), DSPG 20 (Distearoyl Phosphatidylglycerol), DPPG (Dipalmitoyl Phosphatidyglycerol), DEPG (Dielaidoyl Phosphatidyglycerol), DOPG (Dioleoyl Phosphatidyglycerol), DSPA (Distearoyl Phosphatidic Acid), DPPA (Dipalmitoyl Phosphatidic Acid), DEPA (Dielaidoy Phosphatidic Acid), DOPA (Dioleoyl Phosphatidic Acid), DSPS (Distearoyl Phosphatidylserine), DPPS (Dipalmitoyl Phosphatidylserine), 25 DEPS (Dielaidoy Phosphatidylserine), and DOPS (Dioleoyl Phosphatidylserine), or any mixtures thereof.

According to some embodiments, a cationic liposome may be used. Exemplary cationic lipids include, without limitation, stearylamine (SA), lauryltrimethylammonium bromide; cetyltrimethylammonium bromide, myristyl trimethylammonium bromide, dimethyldioctadecylammonium bromide (DDAB), 3β-[N—(N',N'-dimethylaminoethane)-carbamoyl]cholesterol (DC-Cholesterol), 1,2-ditetradecanoyl-3-trimethylammonium-propane (DMTAP), 1,2-dioctadecanoyl-3-trimethylammonium-propane (DOTAP) and DOTAP derivatives such as 1,2-di-(9Z-octadecenoyl)-3-trimethylammonium-propane and 1,2-dihexadecanoyl-3-trimethylammonium-propane, 1,2-di-(9Z-octadecenoyl)-3-dimethylammonium-propane (DODAP) and DODAP derivatives such as 1,2-ditetradecanoyl-3-dimethylammonium-propane, 1,2-dihexadecanoyl-3-dimethylammonium-propane, and 1,2-dioctadecanoyl-3-dimethylammonium-propane, 1,2-di-O-octadecenyl-3-trimethylammonium propane (DOTMA), 1,2-dioleoyl-c-(4'-trimethylammonium)-butanoyl-sn-glycerol (DOTB), dioctadecylamide-glycylspermine, SAINT-2, polycationic lipid 2,3-dioleyloxy-N-[2(spermine-carboxamido)ethyl]-N,N-dimethyl-1-propanaminiumtrifluoroacetate (DOSPA), and GL67™. The cationic lipids may also constitute derivatives of the foregoing. Additional examples of cationic lipids and lipid components may be found in or made according to U.S. Pat. No. 4,804,539 issued to Guo et al, which is incorporated herein by reference. According to some embodiments, the liposomes may contain about 10-40 (i.e., about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40) mole percent of an amine-derivatized lipid component in which a charged amine group is spaced from a lipid polar head region by a carbon-containing spacer arm at least 3 atoms in length. According to some embodiments, the liposomes have a close packed lipid structure produced by inclusion of between 20-50 (i.e., about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50) mole percent of cholesterol or an amine-derivatized cholesterol, and/or phospholipids with predominantly saturated acyl chain moieties. According to some embodiments, the liposomes may be suspended in an aqueous medium containing a high-viscosity polymer, formulated in paste form, or embedded in a polymer matrix, to further enhance liposome retention.

Polymers can also be used for controlled or delayed type release procedures (Langer, Accounts Chem. Res. 26:537, 1993). For example, the block copolymer, polaxamer 407 exists as a viscous yet mobile liquid at low temperatures but forms a semisolid gel at body temperature. It has been shown to be an effective vehicle for formulation and sustained delivery of recombinant interleukin-2 and urease (Johnston et al, Pharm. Res. 9:425, 1992; Pec, J. Parent. Set Tech. 44(2):58, 1990). Alternatively, hydroxyapatite has been used as a microcarrier for controlled release of proteins (Ijntema et al, Int. J. Pharm. 112:215, 1994). Other illustrative and exemplary polymers utilized either alone, in combination, in association with a liposome, or as a polymersome, may include for example, Poly(ethylene glycol) (PEG/PEO), Poly(2-methyloxazoline), Polydimethylsiloxane (PDMS), Poly(caprolactone (PCL), Poly(lactide) (PLA), Poly(methyl methacrylate) (PMMA), povidone, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., EUDRAGIT® L30D55, EUDRAGIT® FS30D, EUDRAGIT® L100, KOLLICOAT® EMM30D, ESTACRYL® 30D, COATERIC®, and AQUATERIC®). The foregoing is not a comprehensive and exhaustive list, and there are other polymeric materials that would meet the objectives of the described invention of providing for a controlled or delayed type release profile of the active therapeutic agent from the skin.

Delivery System Containing Pharmaceutical Compositions

According to some embodiments, the therapeutic agent and/or active metabolite remains in the skin and does not enter the bloodstream.

According to some embodiments, the chemical drivers methylsulfonylmethane (MSM), an amino benzoate local anesthetic, and ethoxydiglycol work together cooperatively and synergistically to deliver the active therapeutic agent.

MSM (formula $(CH_3)2SO_2$), also known as DMSO2, methyl sulfone, and dimethyl sulfone. CAS Registry Number 67-71-0) is an organosulfur compound, and as shown in Formula (I), is a polar molecule having two oxygen atoms that can readily interact with positively charged atoms or molecules.

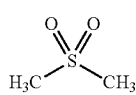

(I)

According to some embodiments, MSM can be administered in a maximum daily dose of up to 6 g/day; according to some embodiments MSM is present as from 1-10 w/w of the pharmaceutical composition, i.e., 1%, 2%, 3%, 4%, 5%, 6%, 7%, 8%, 9%, or 10% w/w of the pharmaceutical composition.

Research in animal models indicates MSM has a very low toxicity when administered topically (see Liu, P. et al., "Metal Chelator combined with permeability enhancer ameliorates oxidative stress-associated neurodegeneration in rat eyes with elevated intraocular pressure," Free Radic. Biol. Med. 69: 289-99 (2014)).

Zhang and coworkers determined that MSM functions as a permeability enhancer and an excipient to facilitate transport of the chelator EDTA (Mw=292.24 g/mol) across biologic membranes, and to make possible localized and regional chelation. Topical application of MSM with $C^{14}$ EDTA onto the rat cornea led to an uptake of the $C^{14}$ EDTA in all tested ocular tissues. Without MSM, EDTA did not penetrate the eye. Additionally, Zhang and co-workers suggested that MSM could also be an adjuvant for delivering ciprofloxacin and other chemical compounds to specific, local tissue sites (See "Assessment of methylsulfonylmethane as a permeability enhancer for regional EDTA chelation therapy"; Drug Delivery; Vol. 16; Pages 243-248, 2009), the disclosure of which is incorporated by reference.

(I)

Ethoxydiglycol (also known as diethylene glycol monoethyl ether having formula $CH_3CH_2OCH_2CH_2OCH_2CH_2OH$) 2-(2-ethoxyethyoxy) ethanol, CAS Registry Number 111-90-0) is a low molecular weight cosmetic grade synthetic solvent and viscosity decreasing agent used in cosmetics and personal care products to ensure even distribution of the ingredients throughout a product. Glycols are a class of alcohols that contain two hydroxyl groups, and are also called a diols. According to some embodiments, ethoxydiglycol is present in a range of 0.10-5% w/w of the pharmaceutical composition, i.e., 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5% w/w of the pharmaceutical composition.

According to some embodiments, the molecular weight of the therapeutic agent of the described invention is less than 500 Da.

The cumulative effect of these three components together is more than additive. As such, lower amounts of each component can be used than would normally be used alone to deliver an active therapeutic agent. According to some embodiments, the chemical drivers enhance delivery of active therapeutic agents having a molecular weight of less than 500 Da. According to some embodiments, the chemical drivers may also be able to enhance delivery of active therapeutic agents having a molecular weight higher than 500 Da.

According to some embodiments, the synergistic effect of the MSM, amino benzoate local anesthetic, and ethoxydiglycol, is effective to provide increased speed to anesthesia, and a reduction of the amino benzoate local anesthetic and the therapeutic agent concentration because of improved penetration of the stratum corneum resulting in effective analgesia.

According to some embodiments, the amino benzoate local anesthetic blocks nerve signals where applied. According to some embodiments, the chemical drivers are effective to increase percutaneous perfusion wherein heat, pH and the polarity of the chemical drivers are factors that affect percutaneous perfusion.

Exemplary amino benzoate local anesthetics include, without limitation, lidocaine (1-10%, i.e., 1%, 2%, 3%, 4%, 5%, 6%, 7%, 8%, 9%, or 10%) w/w of the composition), benzocaine (5-20% (i.e., 5%, 6%, 7%, 8%, 9%, 10%, 11%, 12%, 13%, 14%, 15%, 16%, 17%, 18%, 19% or 20%) w/w of the composition), and tetracaine (2% w/w of the composition). Alternatively, any other suitable local anesthetic can be used including, without limitation, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or a pharmaceutically acceptable salt thereof, or a mixture thereof. Amide type local anesthetics are characterized by an amide functionality, while ester type local anesthetics contain an ester functionality. Exemplary amide type local anesthetics include bupivacaine, prilocaine, mepivacaine, etidocaine, ropivacaine, dibucaine, and mixtures thereof. Exemplary ester type local anesthetics include procaine, chloroprocaine, their pharmaceutically acceptable salt, or a mixture thereof.

According to some embodiments, the amino benzoate local anesthetic is lidocaine (or lidocaine HCl), also known as 2-(diethylamino)-N-(2,6-dimethylphenyl)acetamide shown in Formula (II).

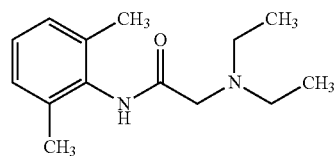

(II)

Lidocaine can be administered in amounts of 0.5 to 4.5 mg/kg/dose (i.e., 0.5, 1.0, 1.5, 2.0, 2.5, 3.0, 3.5, 4.0, or 4.5 mg/kg/dose). The lidocaine can be in the form of viscous lidocaine 2% w/w generally used to treat sore throat, teething, mouth or esophageal sores, or swelling inside the mouth. Viscous lidocaine can also be used to prevent gagging during dental procedures. Lidocaine spray 4% w/w can be used under "crash" circumstances, where speed is of the essence. Lidocaine spray is generally used when a breathing tube is inserted down the larynx during intubation to numb the gag reflex. Combined with the other components of the topical composition for fast anesthesia, time to perform intubation can be decreased where even a few seconds reduced can save a life. Lidocaine spray can also be used during childbirth. Lidocaine spray is commercially available as a 10% w/w solution, and the maximum dose per day is 30 mg within 30 minutes.

Other amino benzoate local anesthetics with similar dosing to lidocaine include tetracaine (2-(dimethylamino)ethyl 4-(butylamino)benzoate), shown in Formula (III), and benzocaine (ethyl 4-aminobenzoate), shown in Formula (IV).

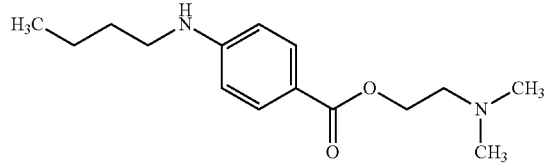

(III)

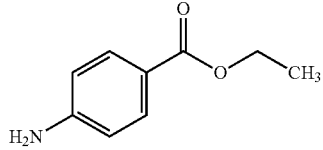

(IV)

Exemplary active therapeutic agents may include without limitation, analgesic agents, wound healing agents, anti-inflammatory agents (steroidal and non-steroidal); anti-oxidant agents; antihistamines or anti-neoplastics either singly or as a combination thereof.

According to some embodiments, the active agent of the topical composition of the described invention can be an analgesic agent. Exemplary analgesics may include the following molecules but not limited to non-steroidal anti-inflammatory drugs (NSAIDS), e.g., paracetamol (acetaminophen), ibuprofen, naproxen, and, COX-2 inhibitors, opioids, flupirtine, and specific agents including, but not limited to tricyclic antidepressants, such as amitriptyline, nefopam, and anticonvulsants, including carbamazepine, gabapentin, and pregabalin.

According to some embodiments, the active agent of the topical composition of the described invention is an antineoplastic agent. Exemplary anti-neoplastics may include, without limitation 5-fluorouracil, temozolomide, busulfan, ifosamide, melphalan, carmustine, lomustine, mesna, capecitabine, gemcitabine, floxuridine, decitabine, mercaptopurine, pemetrexed disodium, methotrexate, vincristine, vinblastine, vinorelbine tartrate, paclitaxel, docetaxel, ixabepilone, daunorubicin, epirubicin, doxorubicin, idarubicin, amrubicin, pirarubicin, mitoxantrone, etoposide, etoposide phosphate, teniposide, mitomycin C, actinomycin D, colchicine, topotecan, irinotecan, gemcitabine cyclosporin, verapamil, valspodor, probenecid, biricodar, terfenadine, quinidine, and pervilleine A.

According to some embodiments, the active agent of the topical composition of the described invention comprises an anti-inflammatory agent. Non-limiting examples of non-steroidal anti-inflammatory agents include, ibuprofen (Advil®), naproxen sodium (Aleve®), and acetaminophen (Tylenol®), oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, can be used for topical application.

Non-limiting examples of steroidal anti-inflammatory agents include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

According to some embodiments, the active agent of the topical composition of the described invention comprises an anti-oxidant agent. Exemplary anti-oxidants may include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

According to some embodiments, the antioxidant may be alpha tocopherol (Vitamin-E), ascorbic acid, ascorbic acid esters, glutathione, lipoic acid, uric acid, carotenes, propyl gallate, sodium bisulfite, sodium sulfite, butylated hydroxytoluene (BHT), butylated hydroxyanisole (BHA), or cysteine.

According to some embodiments, the active agent of the topical composition of the described invention comprises an antihistamine. Non-limiting examples of antihistamines include, without limitation, chlorpheniramine, brompheniramine, dexchlorpheniramine, tripolidine, clemastine, diphenhydramine, promethazine, piperazines, piperidines, astemizole, loratadine and terfenadine.

According to some embodiments, the topical composition of the described invention further contains a topical vasoconstrictor as an additional active agent. Non-limiting examples of topical vasoconstrictors include, for example, oxymetazoline, isoproterenol, phenylephrine, norepinephrine, ephedrine, epinephrine, dobutamine, droxidopa, vasopressin, pseudoephedrine. According to some embodiments, the vasoconstrictor is not a substance that causes a dermatitis or other irritation, e.g., epinephrine, synephrine, or ephedrine.

According to some embodiments, the topical composition is characterized by controlled release or delayed release of locally sustained levels of a minimum effective concentration (MEC) of the active agent.

The intensity of effect of a drug (y-axis) can be plotted as a function of the dose of drug administered (X-axis). Goodman & Gilman's The Pharmacological Basis of Therapeutics, Ed. Joel G. Hardman, Lee E. Limbird, Eds., $10^{th}$ Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug. Id. If the active therapeutic agent is to be administered by transdermal absorption, a highly potent active therapeutic agent is required, since the capacity of the skin to absorb active therapeutic agents is limited.

The slope of the dose-effect curve reflects the mechanism of action of a drug. The steepness of the curve dictates the range of doses useful for achieving a clinical effect.

Maximal or clinical efficacy refers to the maximal effect that can be produced by a drug. Maximal efficacy is determined principally by the properties of the drug and its receptor-effector system and is reflected in the plateau of the curve. In clinical use, a drug's dosage may be limited by undesired effects.

Biological variability may exist. An effect of varying intensity may occur in different individuals or subjects at a specified concentration or a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the MEC. Following administration of a dose of drug, its effects usually show a characteristic temporal pattern. A plot of drug effect vs. time illustrates the temporal characteristics of drug effect and its relationship to the therapeutic window. A lag period is present before the drug concentration exceeds the minimum effective concentration (MEC) for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accordingly another dose of drug should be given to maintain concentrations within the therapeutic window.

According to some embodiments, the potency of the active therapeutic agent in the claimed pharmaceutical composition is maintained within a range of from 3 to 5% w/w of the composition i.e., at least 2% w/w of the composition when the local anesthetic is lidocaine; from 10 to 20% (10%, 11%, 12%, 13%, 14%, 15%, 16%, 17%, 18%, 19%, or 20%) w/w of the composition i.e., at least 5% w/w of the composition when the local anesthetic is benzocaine and from 1 to 2% (i.e., 1.0%, 1.1%, 1.2%, 1.3%, 1.4%, 1.5%, 1.6%, 1.7%, 1.8%, 1.9% or 2.0%) w/w of the composition i.e., at least 1% w/w of the composition when the local anesthetic is tetracaine.

According to some embodiments, the concentration of the active therapeutic agent is at least 1% w/w of the composition, at least 2% w/w of the composition, at least 3% w/w of the composition, at least 4% w/w of the composition, at least 5% w/w of the composition, at least 6% w/w of the composition, at least 7% w/w of the composition, at least 8% w/w of the composition, at least 9% w/w of the composition, at least 10% w/w of the composition; at least 11% w/w of the composition; at least 12% w/w of the composition; at least 13% w/w of the composition; at least 14% w/w of the composition; at least 15% w/w of the composition; at least 16% w/w of the composition; at least 17% w/w of the composition; at least 18% w/w of the composition; at least 19% w/w of the composition; at least 20% w/w of the composition, at least 30% w/w of the composition, at least 40% w/w of the composition, at least 50% w/w of the composition, or at least 60% w/w of the composition. According to some embodiments, the concentration of the active agent is from about 1% to about 10% w/w of the composition, i.e., at least 1%, at least 2%, at least 3%, at least 4%, at least 5%, at least 6%, at least 7%, at least 8%, at least 9%, or 10% w/w of the composition when the local anesthetic is lidocaine. According to some embodiments, the concentration of the active agent is from about 5% to about 20% w/w of the composition, i.e., at least 5%, at least 6%, at least 7%, at least 8%, at least 9%, at least 10%, at least 11%, at least 12%, at least 13%, at least 14%, at least 15%, at least 16%, at least 17%, at least 18%, at least 19% or 20% w/w of the composition when the local anesthetic is benzocaine. According to some embodiments, the concentration of the active agent is from about 1% to about 2% w/w of the composition, i.e. at least 1%, or 2% w/w of the composition when the local anesthetic is tetracaine.

According to some embodiments, the content of the active agent retained on skin and its permeation/flux into the skin can be measured as a function of time. According to some embodiments, flux is determined using one of many available artificial membranes attached to a Franz diffusion cell. According to some embodiments, permeation and retention are determined using human cadaver skin attached to a Franz diffusion cell. According to some embodiments, the retained concentration is correlated to the minimum effective concentration.

According to some embodiments, the pharmaceutical composition can be applied directly to the skin.

The pharmaceutical composition may further include auxiliary agents, e.g., lubricants, preservatives, stabilizers, wetting agents, emulsifiers, salts for influencing osmotic pressure, buffers, colorants, flavorants and/or fragrances and the like which are compatible with the active compounds, carriers, excipients, flocculants, penetration enhancers, plasticizers, pH balancers, moisturizers, emollients, surfactants and emulsifiers, bactericides, thickening agents, softening agents, etc.

The composition can also include agents that assist in maintaining the molecular structure integrity of the therapeutic or help deliver the therapeutic agent through the skin, such as but not limited to solvents that break down lipophilic therapeutics or adjust ionic charge for easier delivery into skin, detergents such as but not limited to anionic detergents (e.g., alkylbenzenesulfonates), cationic detergents, non-ionic detergents (e.g., ethoxylates, PEGylates), or zwitterionic detergents (3-[(3-cholamidopropyl)dimethylammonio]-1-propanesulfonate)), cyclodextrins that readily complex with lipophilic therapeutics like steroids, including cc-cyclodextrin, β-cyclodextrin, and γ-cyclodextrin, other complexing agents (i.e. chelating agents with two or more separate coordinate bonds between a multiple bonded ligand and a central atom (metal), such as, but not limited to, glutamic acid, histidine, malate, phytochelatin, hemoglobin, chlorophyll, ethylenediaminetetraacetic acid (EDTA), amino acid chelates, and dimercaprol), and other amphipathic chemicals.

Exemplary plasticizers include, without limitation, phthalic anhydride esters, esters of adipic acid, epoxidized esters, trimellitic esters, triacetin, N-methyl-2-pyrrolidone, glycerol formaldehyde, triethyl citrate (TEC), acetyltributylcitrate, ethanol, and polyethylene glycol.

Non-limiting examples of penetration enhancers include propylene glycol (PG), dimethylsulfoxide (DMSO), dimethyl formamide (DMF), allantoin, urazole, N,N-dimethylacetam ide (DMA), decylmethylsulfoxide (C10 MSO), polyethylene glycol monolaurate (PEGML), propylene glycol monolaurate (PGML), glycerol monolaurate (GML), lecithin, the 1-substituted azacycloheptan-2-ones, e.g., 1-n-dodecylcyclazacycloheptan-2-one (available under the trademark Azone® from Whitby Research Incorporated, Richmond, Va.), alcohols, and the like. The penetration enhancer may also be a vegetable oil, for example, safflower oil, cottonseed oil and corn oil. Additional penetration enhancers may generally be found in Remington's Pharmaceutical Sciences, 18th or 19th editions, published by the Mack Publishing Company of Easton, Pa. which is incorporated herein by reference.

Exemplary anti-oxidants may include the following, but not limited to, ascorbic acid and glutathione (GSH) etc. According to some embodiments, the antioxidant agent is present at a concentration from 10%-20% (i.e., 10%, 11%, 12%, 13%, 14%, 15%, 16%, 17%, 18%, 19% or 20%) w/w of the composition for ascorbic acid and from 2%-5% (i.e., 2%, 2.1%, 2.2%, 2.3%, 2.4%, 2.5%, 2.6%, 2.7% 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5%) for glutathione.

Surfactants are organic compounds that are amphiphatic, containing both hydrophobic groups and hydrophilic groups. Surfactants include, but are not limited to anionic surfactants, cationic surfactants and non-ionic surfactants.

Anionic surfactants include fatty acid soaps (including sodium oleate, sodium palmitate, sodium myristate, sodium sterate, potassium oleate and triethanolamine oleate); alkyl sulfates (including sodium dodecyl sulfate, ammonium lauryl sulfate, triethanolamine lauryl sulfate and sodium alkyl sulfate); alkyl lactylates (including calcium stearoxyl-2-lactylate), alkyl lactates (including sodium-O-stearyllactate and sodium stearoyllactylate) alkyl benzenesulfonates (including calcium dodecyl benzene sulfonate); alkyl sulfonates (including alkyl aryl sulfonate); alkyl phosphates; alkyl oleates; alkyl stearates (including self-emulsifying glycerol monostearate); alkyl esters (including dioctyl ester of sodium sulphosuccininc acid (AOT, Aerosol OT); acyl sulfates; or acyl sulfosuccinates.

Cationic surfactants include alkyl primary, secondary, tertiary, or quaternary amines; high-molecular-weight amine and fatty amine blends; polyoxyethylene fatty amines (including tallow amine); alkyl sulfates (including N-cetyl-N-ethyl morpholinium ethyl sulfate (35%)); alkyl pyridinium and quaternary ammonium salts.

Non-ionic surfactants include alcohol ethoxylate, alkylphenol ethoxylate, fatty acids (such as oleic acid), lanolin alcohols (such as polyoxyethylene (5) lanolin alcohol (ether and ester), polyoxyethylene (50) lanolin (ether and ester), acetylated polyoxyethylene (10) lanolin, polyoxyethylene (16) lanolin alcohol, acetylated polyoxyethylene (9) lanolin), alkyl polyglycosides, mono-, di- or glyceride esters (such as diglycerine sesquioleate), acetylated monoglycerides, polyglycerols, polyglycerol esters (such as decaglycerol decaoleate, decaglycerol octaoleate, decaglycerol tetraoleate), phospholipids (such as lecithin), mono- or diglyceride esters of citric acid, tartaric acid and lactic acid, sorbitan fatty acid esters (such as sorbitan monostearate (Span 60, Crill 3), sorbitan monooleate (Arlacel 80, Span 80, Crill 4), sorbitan isosterate (Crill 6), sorbitan monolaurate (Arlacel 20, Span 20, Crill 1), sorbitan trioleate (Span 85, Crill 45), sorbitan tristearate (Span 65), sorbitan sesquioleate (Arlacel 83, Crill 43), sorbitan monopalmitate (Span 40, Crill 2)), polyol fatty acid esters (such as ethylene glycol distearate, ethylene glycol monostearate, diethylene glycol monostearate, propylene glycol monostearate, propylene glycol monolaurate, polyoxyethylene (1.5) nonylphenol, polyoxyethylene (4) nonylphenol, polyoxyethylene (5) nonylphenol, polyoxyethylene (6) nonylphenol, polyoxyethylene (8) nonylphenol, polyoxyethylene (20) nonylphenol, polyoxyethylene (30) nonylphenol, polyoxyethylene (10) nonylphenol, poly(ethylene glycol) 200 distearate, poly(ethylene glycol) 300 dilaurate, poly(ethylene glycol) 400 distearate, polyoxyethylene octylphenol, poly(ethylene glycol) 400 dilaurate, poly(ethylene glycol) 400 monostearate, poly(ethylene glycol) 400 monolaurate, poly(ethylene glycol) 4000 distearate, polyoxyethylene (10) octylphenol, poly(ethylene glycol) 600 monostearate, Polyoxyethylene (14) nonylphenol, polyoxyethylene (24) cholesterol, polyoxyethylene (25) soyasterol, poly(ethylene glycol) 1000 monooleate, polyoxyethylene (25) propylene glycol monostearate, poly(ethylene glycol) 1000 monolaurate, polyoxyethylene (70) dinonylphenol), glycerol fatty acid esters (such as glycerol dioleate, glycerol monoleate, glycerol monostearate, glycerol monolaurate, polyoxyethylene (20) glycerol monostearate), sucrose fatty acid esters (such as sucrose distearate, sucrose monolaurate), polyoxyethylene sorbitan fatty acid esters (polysorbates) (such as polyoxyethylene (4) sorbitan monolaurate, polyoxyethylene (5) sorbitan monooleate, polyoxyethylene (20) sorbitan monooleate (Tween 80), polyoxyethylene (40) sorbitol hexaoleate, polyoxyethylene (50) sorbitol hexaoleate, polyoxyethylene (20) sorbitan tristearate, polyoxyethylene (20) sorbitan trioleate, polyoxyethylene (20) sorbitan monostearate, polyoxyethylene (20) sorbitan monopalmitate, polyoxyethylene (20) sorbitan monolaurate (Tween 20), polysorbate 20 NF, EP, JP, poly(ethylene glycol)-20 sorbitan isostearate, poly(ethylene glycol) (20) sorbitan trioleate (Crillet 45), poly(ethylene glycol) (20) sorbitan stearate (Crillet 3 Super, Polysorbate 60), poly(ethylene glycol) (20) sorbitan oleate (Crillet 4 Super, Polysorbate 80), poly(ethylene glycol) (20) sorbitan laurate (Crillet 2 Super, Polysorbate 40)), monoesters (such as polyoxyethylene (4) stearic acid, polyoxyethylene (8) stearic acid, polyoxyethylene (8) lauric acid, polyoxyethylene (40) stearic acid, polyoxyethylene (50) stearic acid), polyethoxylated esters of acyl acids (such as polyoxyethylene (2) octyl alcohol, polyoxyethylene (4) tridecyl alcohol, polyoxyethylene (6) tridecyl alcohol, polyoxyethylene (8) tridecyl alcohol), copolymers of polyethylene oxide and polypropylene oxide, polyoxyethylene fatty ethers (such as polyoxyethylene fatty ethers derived from lauryl, cetyl, stearyl and oleyl alcohols, polyoxyethylene (4) lauryl ether, polyoxyethylene (23) lauryl ether (Brij 35), polyoxyethylene (2) cetyl ether (Brij 52), polyoxyethylene (10) cetyl ether, polyoxyethylene (20) cetyl ether (Brij 58), polyoxyethylene (2) stearyl ether (Brij 72), polyoxyethylene (10) stearyl ether, polyoxyethylene (20) stearyl ether, polyoxyethylene (2) oleyl ether, polyoxyethylene (10) oleyl ether (Brij 97), polyoxyethylene (20) oleyl ether, polyoxyethylene (21) stearyl ether, polyoxyethylene (12) lauryl ether), fatty amides (such as N,N,-Dimethylstearamide), Polyethylene glycol ether of linear alcohol, polyoxyethylene (15) tall oil fatty acids (ester), acetylated sucrose diesters, isopropyl ester of lanolin fatty acids, polyoxyethylene sorbitol beeswax derivative, Polyoxypropylene/Polyoxyethylene condensate, sodium oleate, polyoxyethylene (20) castor oil (ether, ester), glycerol oleate & propylene glycol (Arlacel 186) and Cremophor.

Exemplary pharmaceutical carriers also include starch, glucose, lactose, sucrose, gelatin, saline, gum acacia, keratin, urea, malt, rice flour, chalk, silica gel, sodium stearate, glycerol monostearate, talc, sodium chloride, dried skim milk, glycerol, propylene, glycol, water, and ethanol. If desired, the carrier can also contain minor amounts of wetting or emulsifying agents, or pH buffering agents.

Formulations for topical application can take the compositional form of a liquid, a semisolid dosage form (e.g., a paste, a cream, a lotion, a powder, an ointment or a gel), a patch or a spray. According to some embodiments, the topical composition may be a cream or gel that can be applied to an affected area of the skin of a subject in need thereof. Different release profiles can be achieved with different forms, such as but not limited to controlled release, delayed release, extended release, or sustained release. The topical pharmaceutical composition may be applied multiple times a day, once per day, or as often as needed.

According to some embodiments, an exemplary pharmaceutical cream formulation may include: Lidocaine (local anesthetic agent), MSM (chemical driver), ethoxydiglycol (chemical driver), deionized water, polyacrylamide (a flocculant), C13-14 isoparaffin (an emollient), laureth-7 (surfactant and emulsifier), propylene glycol (penetration enhancer), triethanol amine (pH balancer), emu oil (antifungal agent), tea tree oil (antifungal agent), *Arnica montana* extract (anti-inflammatory agent); ethylhexylglycerin (fragrant), phenoxyethanol (bactericide), isopropyl palmitate (emollient, moisturizer, thickening agent, anti-static), stearic acid (surfactant and softening agent), 5-fluorouracil (antineoplastic). Any suitable excipients in these categories also can be used in accordance with the embodiments of the described invention.

Lidocaine is a widely used local anesthetic that was first synthesized by Lofgren in 1943 (Lofgren N, Lundqvist B (1946). Svensk Kemisk Tidskrift 58: 206-17). Its IUPAC name is: 2-(diethylamino)-N-(2,6-dimethylphenyl) acetamide, and its CAS number is: 137-58-6/73-78-9 (hydrochloride). Lidocaine is used as a topical pain reliever/numbing agent in both prescription and over the counter (OTC) forms (Drug Bank. (2013, Feb. 8). Lidocaine. http://drugbank.ca/drugs/DB00281, accessed 28 Aug. 2013), may be used as an injected local anesthetic during various surgical procedures, and also is used intravenously in certain circumstances, such as in cardiac arrest. Lidocaine also is a first line anti-arrhythmic drug when used at high doses (Sleight P J (1990). Cardiovasc Pharmacol 16: S113-119); (Collinsworth, K. Circulation 50: 1217-30 (1974). In addition, lidocaine is often the local anesthetic of choice during intubation, minimally invasive surgery, and many dental procedures (Mehta P, Caiazzo A, Maloney P (1998). Anesth Prog 45: 38-41).

The effectiveness of lidocaine as a local anesthetic is distinguished by its accelerated onset of action and intermediate duration. As a result, lidocaine is suitable for infiltration, block and surface anesthesia (Alabdalla J, Hoffart L. *Lidocaine*. http://www.lidocaine.weebly.com/references.htm, accessed 27 Aug. 2013). While lidocaine's mechanism of action is favorable for multiple modes of anesthesia, the ability of a formulation to allow adequate dermal penetration has limited the utility of topical lidocaine treatments. The study of cutaneous barriers to topical absorption suggests that hydrophobicity has little impact on the ability of a topically applied drug to reach interstitial fluid (Fortenbach C R, Modjtahedi B S, Maibach H I (2008). Skin Pharmacol Physiol 21: 294-299); (Hansen S, Lehr C M, Schaefer U F (2013). Adv Drug Deliv Rev 65: 251-264). However, it has also been noted that greater lipid solubility results in increased diffusion through cell membranes, and thereby slowing the onset of anesthesia (in the case of anesthetics) (Becker D E, Reed K L (2012). Anesth Prog 59: 90-102). In the case of drugs bearing charged groups, as with the tertiary amines of lidocaine and related substances, transfer efficiency into circulation is related to the pKa of the charged group, where a pKa of 7.4 or slightly below providing greater entry into neuronal cell membranes and thus greater anesthetic efficiency. Other studies have indicated that dosing with other agents such as epinephrine, can increase the concentration of lidocaine in the brain (Takahashi R, Oda Y, Tanaka K, Morishima H O, Inoue K, Asada A (2006). Anesthesiol 105: 984-989). Because there appears to be a strong linear correlation between the concentration of a drug in serum and in interstitial fluid, the ability to provide efficient transdermal drug delivery has significant clinical implications (Jepps O G, Dancik Y, Anissimov Y G, Roberts M S (2013). Adv Drug Deliv Rev 65: 152-168). Indeed, several groups have reported on formulations intended to enhance topical drug delivery (Lee P J, Ahmad N, Langer R, Mitragotri S, Shastri V P (2006). Intl J Pharmaceut 308: 33-39); (Roberts M S, Cross S E (1999). Inflammopharmacol 7: 339-50); (Osborne D W (2011). J Cosmet Dermatol 10: 324-9); (Otto A, Wiechers J W, Kelly C L, Hadgraft J, du Plessis J (2008). Skin Pharmacol Physiol 21: 326-334). To take advantage of the potential benefits from topical drug application, a unique, proprietary formulation of lidocaine has been developed by Sam bria Pharmaceutical, focusing on agents that act as the "drivers" of cutaneous penetration. Our studies suggest that this formulation for lidocaine provides excellent results in providing anesthetic effects for local, acute pain.

Along with providing direct delivery to interstitial fluid, there are a number of advantages and disadvantages to using a topical pain relief cream. Advantages include, but are not limited to, avoidance of hepatic first-pass metabolism, convenience and ease of application, and the ability to target a specific site of pain. Disadvantages may include skin irritation, and also may include poor or variable permeability through the skin, which can result in insufficient therapeutic effect for the patient (Moody M L (2010). Topical Medications in the Treatment of Pain. New York City: McMahon Publishing).

As shown in Table 1, the amount of used deionized water would then accordingly be chosen in the pharmaceutical formulation such that the final amount w/w % will be equal to 100%:

TABLE 1

Exemplary cream formulation.

| Specific Ingredient | Amount (w/w %) | Range (w/w %) |
|---|---|---|
| Deionized water | Can be varied | 1-50% |
| Lidocaine | 4.00% | 1-20% |
| MSM | 3.00% | 1-10% |
| Ethoxydiglycol | 1.00% | 0.10-5% |
| Polyacrylamide | 6.50% | 1-20% |
| $C_{13-14}$ isoparaffin | 6.50% | 1-20% |
| Laureth-7 | 6.50% | 1-20% |
| Propylene Glycol | 1.00% | 0.10-5% |
| Triethanolamine | 0.90% | 0.10-5% |
| Emu Oil | 0.25% | 0.10-5% |
| Tea Tree Oil | 0.20% | 0.10-5% |
| Arnica Montana Extract | 0.50% | 0.10-5% |
| Ethylhexylglycerin | 0.40% | 0.10-5% |
| Phenoxyethanol | 0.40% | 0.10-5% |
| Isopropyl Palmitate | 0.20% | 0.10-5% |
| Stearic Acid | 0.15% | 0.05%-5% |
| 5-fluorouracil | 1.00% | 1.00%-5% |

According to some embodiments, formulations and doses can be tailored to a subject's fat content, as some therapeutic can be lost to the fat layer (the rate and extent of the diffusion of the therapeutic and amino benzoate local anesthetic can vary).

The pharmaceutical composition of the described invention is administered and dosed in accordance with Good Medical Practice's (GMP's) and guidelines provided and approved by the Food and Drug Administration (FDA), taking into account the clinical condition of the individual subject, the site and method of administration, scheduling of administration, patient age, sex, body weight, whether or not the subject is on other medication and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those having ordinary skill in the art.

Use of the Disclosed Compositions

According to some embodiments, the topical delivery system of the described invention can be used in the manufacture of a medicament for treating a plurality of skin conditions, disorders or diseases. Non-limiting examples of diseases or disorders that can be treated with the pharmaceutical composition of the described invention include, without limitation, pruritus, atopic dermatitis, psoriasis, acne, skin infections, skin infestations, skin neoplasms, wounds to the skin, pain causing disorders and skin manifestations of autoimmune disorders or uses for anesthesia prior to procedures including, but not limited to, for example superficial dermal instrumentation.

According to another aspect, the described invention provides a method for treating a disease, disorder or condition susceptible to treatment topically comprising administering the topical composition described herein to skin.

According some embodiments, the pharmaceutical composition of the described invention can be administered as the pharmaceutical formulation alone, or as an active ingredient in combination with pharmaceutically acceptable carriers, diluents, adjuvants and other auxiliary vehicles. According to some embodiments, the subject is for example, a warm-blooded animal, for example a mammal, including man. The pharmaceutically acceptable carriers, diluents, adjuvants and vehicles, as well as implant carriers generally refer to inert, non-toxic solid or liquid fillers, diluents or encapsulating material not reacting with the active ingredients of the invention.

The doses given may be as a single dose, or as multiple doses over a predetermined period stretching a plurality of days, months or years. As used herein the term "plurality" refers to an event characterized by more than one. According to some embodiments, the pharmaceutical composition is administered multiple times at a plurality of treatment dates, or as needed in the judgment of a treating physician.

According to some embodiments, treatment can be continuous or discontinuous. As used herein, the term "continuous" refers to an activity that is unbroken and without interruption. As used herein, the term "discontinuous" refers to an activity that is broken and with interruption for a predetermined amount of time as judged by the treating physician. As such, the treatment may advantageously be conducted continuously over a period of days, months, or years or discontinuously over a period of days, months, or years.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although exemplary methods and materials have been described, any methods and materials similar or equivalent to those described herein can also be used in the practice or testing of the described invention. All publications mentioned herein are incorporated herein by reference to disclose and described the methods and/or materials in connection with which the publications are cited.

As used herein and in the appended claims, the singular form "a," "and," "the" include plural referents unless the context clearly dictates otherwise. The terms "comprises," "comprising," "includes," "including," "having" and their conjugates mean "including but not limited to." Terms and phrases used in this application, and variations thereof, unless otherwise expressly stated, should be construed as open ended as opposed to limiting. As examples of the foregoing, the term, "including" should be read as meaning "including, without limitation" or the like. The term, "example" is used to provide exemplary instances of the item in discussion, not an exhaustive or limiting list thereof. Adjectives such as e.g., "conventional," "traditional," "known" and terms of similar meaning should not be construed as limiting the item described to a given time period, or to an item available as of a given time, but, instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. The presence of broadening words and phrases such as "one or more," "at least," "such as but not limited to," or other like phrases in some instances shall not be read to mean that the narrower case is intended or required in instances, wherein such broadening phrases may be absent.

Additionally, for example any sequence(s) and/or temporal order of sequence of the system and method that are described herein this disclosure are illustrative and should not be interpreted as being restrictive in nature. Accordingly, it should be understood that the process steps may be shown and described as being in a sequence or temporal order, but they are not necessarily limited to being carried out in any particular sequence or order.

Although the described invention has been described and illustrated herein with referred to some embodiments, it will be apparent to those of ordinary skill in the art that other embodiments may perform similar functions and/or achieve like results. Thus, it should be understood that various features and aspects of the disclosed of the disclosed embodiments can be combined with, or substituted for one another in order to form varying modes of the disclosed invention. Many different embodiments such as variations, adaptations, modifications, and equivalent arrangements thus fall within the scope and spirit of the described invention. Although a specific composition has been described, broader invention that would include some elements are also contemplated herein this disclosure.

The publications discussed herein are provided solely for their disclosure prior to the filing date of the described invention. Nothing herein should be construed as an admission that the described invention is not entitled to antedate such publication by virtue of prior invention. Further, the dates of publication provided may be different from the actual publication dates, which may be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

Example 1 Phase 1 Clinical Study

Objectives of the Study

The primary objective of this Phase Clinical I study was to determine the safety of topically applied NeuroMed7™ 4% lidocaine, as indicated by its uptake into blood and clearance rate and also by the occurrence of latent adverse events.

Secondary objectives included:
- estimating the effectiveness of a proprietary cream formulation;
- determining the effect of dosage frequency on blood levels and clearance rate;
- among patients reporting acute pain, determining the effectiveness of the topical cream in reducing pain, as expressed by self-reported visual analog scale (VAS); and
- estimating rates of absorption and distribution, and also of metabolism by simultaneous determination of lidocaine and of monoethylglycinexylidide (MEGX), the primary metabolite of lidocaine.

Materials and Methods

Ethics:

The study was conducted by the clinical research unit of Insight Institute of Neurosurgery & Neuroscience (Flint, Mich.), in accordance with the guidelines on International Conference on Harmonisation Guidelines for Good Clinical Practice (E6[R1]) (International Conference on Harmonisation Guidelines for Good Clinical Practice (E6[R1]). ich.org/products/guidelines/efficacy/efficacy-single/article/good-clinical-practice.html. Accessed 13 Nov. 2013), the Code of Federal Regulations for Good Clinical Practice (21 CFR Parts 50 and 56) (US Food and Drug Administration. FDA regulations relating to Good Clinical Practice and clinical trials. http://www.fda.gov/scienceresearch/specialtopics/runningclinicaltrials-/ucm 114928. htm. Accessed 13 Nov. 2013), and the Declaration of Helsinki regarding the treatment of human study subjects (WMA Declaration of Helsinki—Ethical principles for medical research involving human subjects. http://wma.net/en/20activities/10ethics/10helsinki/. Accessed 13 Nov. 2013). The clinical study protocol and informed consent form were reviewed and approved (Jul. 30, 2013) by the institutional review board at Western Institutional Review Board (WIRB, Olympia, Wash., study 20131169). All subjects signed informed consent forms prior to enrolling in the study, and were interviewed for latent adverse effects within 24 h after completion of study activities. All study procedures were performed between Aug. 15 and Sep. 22, 2013. All subjects who registered into the study met the eligibility criteria that had been approved by WIRB.

Inclusion Criteria included:
- Healthy individuals of both genders and any ethnic background;
- Age≥18 years;
- Willing to submit to venipuncture at study intervals; and
- Ability to understand and the willingness to sign a written informed consent.

Exclusion Criteria included:
- Cardiac, hepatic, renal, pulmonary, neurological, gastrointestinal and hematological diseases, psychiatric disorders, and allergy to local anesthetics;
- History of chronic disease;
- Pregnancy;
- Active local skin infection or skin pathological condition at the site of administration;
- Tattoo, surgical scar or skin condition at the site of administration that might interfere with penetration of agent into the skin; and
- Currently using lidocaine or any related amide-containing agent that might provide a false positive result in the clinical analysis of lidocaine.

Study Drug:

The lidocaine preparation marketed as NeuroMed7™ was obtained from Sambria™ Pharmaceuticals at 4% (w/w) in a cream that includes methylsulfonylmethane (MSM) and ethoxydiglycol in accordance with the formulation disclosed in Table 1 above.

Drug Application and Safety Sample Analysis:

The 4% lidocaine cream was provided by Sambria Pharmaceuticals (Woodstock, Ga.). Whole blood (10 mL per bleed) was collected using standard venipuncture into serum Vacutainer tubes (Franklin Lakes, Ill.). Following centrifugation at 1000×g for 30 min, serum was transferred to 5 mL polypropylene tubes and snap-frozen in a dry ice/ethanol slurry. Frozen samples were shipped overnight on dry ice to NMS Labs, Willow Grove, Pa. The samples were analyzed by gas chromatography, using forensic standards with a detection limit of 0.1 mcg/mL for both lidocaine and MEGx, ie, 15-20-fold below the therapeutic reference range (NMS Labs, Willow Grove, Pa.) (http://www.pathology.med.umich.edu/handbook/, accessed 6 Sep. 2013). This analytical method was selected to allow quantitation of sub-clinical levels of lidocaine and MEGx that are not captured using standard clinical laboratory methods (typically, fluorescence polarization immunoassay). The selected method also will detect levels of drug that fall within the clinical range, which is necessary to verify the relationship between dosage and physiological response.

Figure 3:
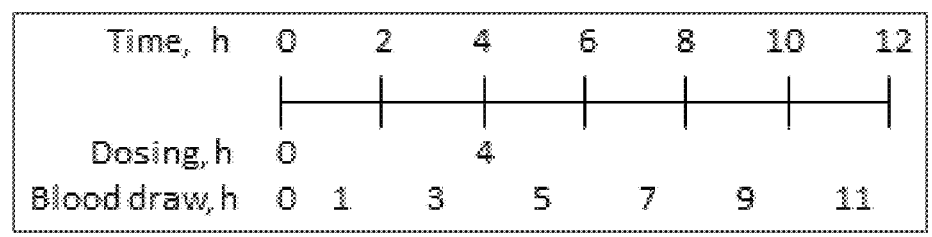
FIG. 3 shows the study schema for the Phase I Clinical Study for determining the uptake kinetics of NeuroMed 7™ pain relief cream composed of lidocaine HCl 4% w/w in base formula with dosing at 0 and 4 hours, and self-reported visual analog scale (VAS); and venous blood draws at 0 (baseline), 1, 3, 5, 7, 9 and 11 hours.

Clinical Study Schema:

The general study plan required 2 equivalent, 1 mL doses of NeuroMed7™ 4% lidocaine to a subject's selected region of acute pain and drug application at 0 and 4 h, with schema presented in FIG. 3. As indicated, 10 mL of venous blood was collected throughout the study period, at time intervals likely to capture peak and trough levels (Greenblatt D J et al. (1985). Arch Otolaryngol 111: 2988-3000); (Baumann L S, et al. (2010). J Drugs Dermatol 9: 1500-1504). Each subject provided self-rated pain evaluations at those same time intervals, focusing on pain at the identified site of acute pain and of drug application, using the 1-10 Visual Analog Scale (VAS) (Meier T, et al. (2003). Pain 106: 151-158).

Results and Discussion

Safety Study:

The primary goal of this Phase I study was to investigate the extent to which lidocaine enters circulation following topical application of NeuroMed7 4% lidocaine cream, to indicate drug safety. Blood levels frequently are used as an index of toxicity, particularly in the absence of physiological signs. There are clinical signs that indicate the presence of adverse effects due to relatively high levels of lidocaine, and also of some physiologically active degradation products, in particular, MEGx. This study used both blood measurements, and questions posed to study subjects on specific side effects, as indicators of NeuroMed7™ safety.

Venous blood samples were taken prior to the initial dosing at 0 h, and 1, 3, 5, 7, 9 and 11 hours following the initial (1 h) drug application, which for the last 4 samples (indicated on FIG. 3. Study Schema) also corresponds to 1, 3, 5 and 7 hours after the second (4 h) drug application. Lidocaine levels were below the detection limit of 0.1 mcg/mL (μg/mL) in all blood samples. Among all samples analyzed for MEGx, only one, sample #4 for subject 16, the level of MEGx was at the detection limit, i.e., 0.1 mcg/mL. Given that the anticipated peak levels in blood occur between 1 and 2 hours after administration, and the unlikelihood of consenting subjects to more frequent venipuncture, the study was designed to approximate the peak drug levels resulting from each lidocaine dose.

For these blood analytes, among 239 serum samples that were analyzed, only 1 displayed a measurable result, despite our use of an analytical method that is 15-20-fold more sensitive than typical clinical laboratory methods that are calibrated for therapeutic levels ranging from 1.5 to 5.0 mcg/mL (http://www.mayomedicallaboratories.com/test-catalog/Clinical+and+Interpretive/8382. Accessed 19 Nov. 2013); (Becker D E, Reed K L (2012). Anesth Prog 59: 90-102). The one detectable sample was collected 1 h after the second lidocaine administration, and results from the additive effect of the subject's initial dose along with the 4 h dose. It is concluded from toxicology studies that the doses of lidocaine in NeuroMed7™, used as indicated in the FDA monograph, are well below the levels of concern.

Toxic levels of lidocaine typically occur at levels greater than 6.0 mcg/m L, with symptoms including central nervous excitation, lightheadedness, dizziness, tinnitus, confusion, and blurred or double vision (Valdes R et al. (1998). Clin Chem 44(5): 1096-1099). Within 24 h after concluding the study, as well as during their immediate participation, subjects were contacted with questions regarding side effects. There were no such reports of adverse effects related to drug activity. Three subjects did experience slight lightheadedness that appeared to result from venipuncture, as they were felt after each blood draw. It is concluded from the measured blood levels, as well as clinical signs, that the subjects in this study expressed no symptoms of lidocaine toxicity.

Figure 4:
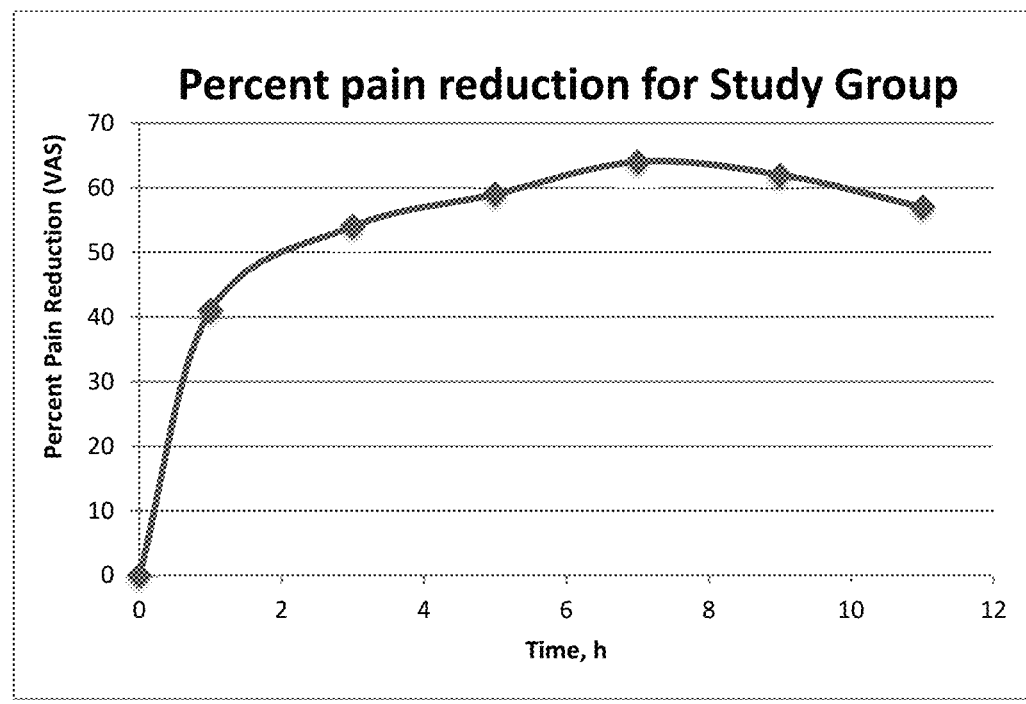
FIG. 4 shows the percentage of pain reduction for the study subjects.
Figure 5:
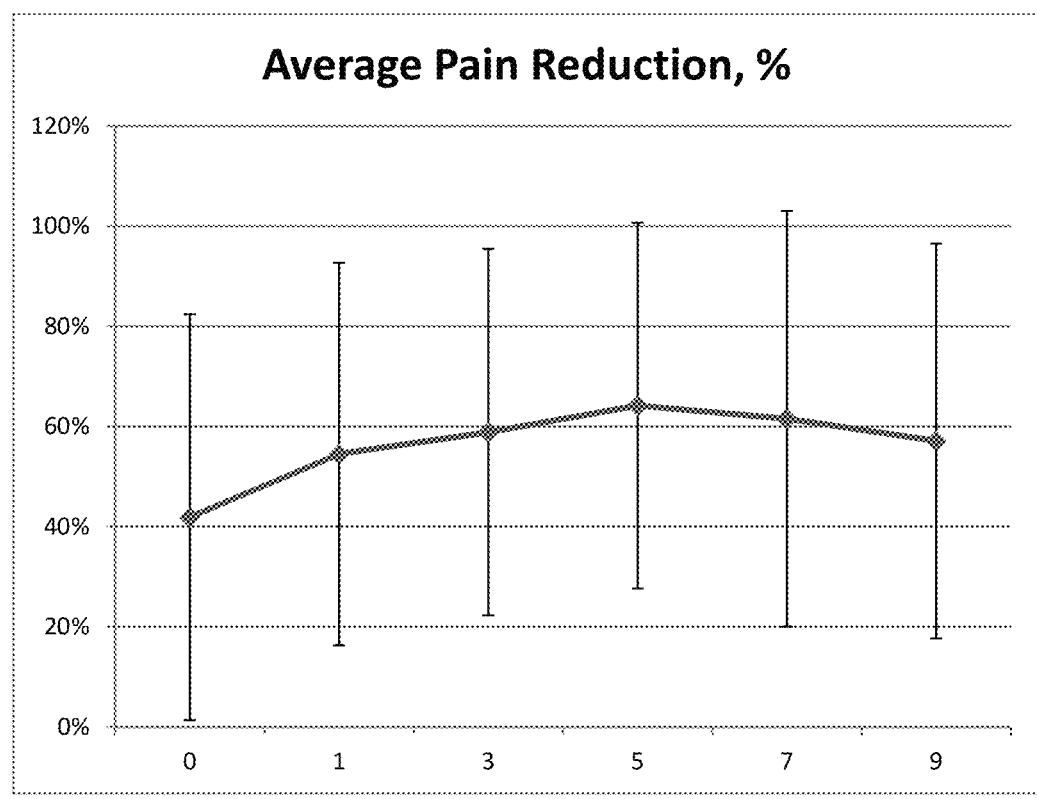
FIG. 5 shows the average pain reduction for the study subjects.

Studies of Efficacy:

The central data used to describe efficacy was the 10-point VAS. While this measure is subjective, the study subjects were requested specifically to be consistent in their pain estimates. The mean initial pain score at 0 h (+/−SD) was 4.0 (1.3). The reported pain reduction for all subjects and at all time points was significant and transient, as expected (FIG. 4). The subjective nature self-scored pain scales, noted with VAS, as well with other pain scales, results in considerable subject-to-subject variation. This is particularly dramatic when looking at the variation (expressed as standard deviation) in the average pain reduction within the study cohort (FIG. 5). Having such a broad range results from the inherent subjectivity of the initial pain score, compounded by the subjective estimate in efficacy. Regardless of specific numbers, NeuroMed7™ had a positive effect in reducing acute pain.

Figure 6:
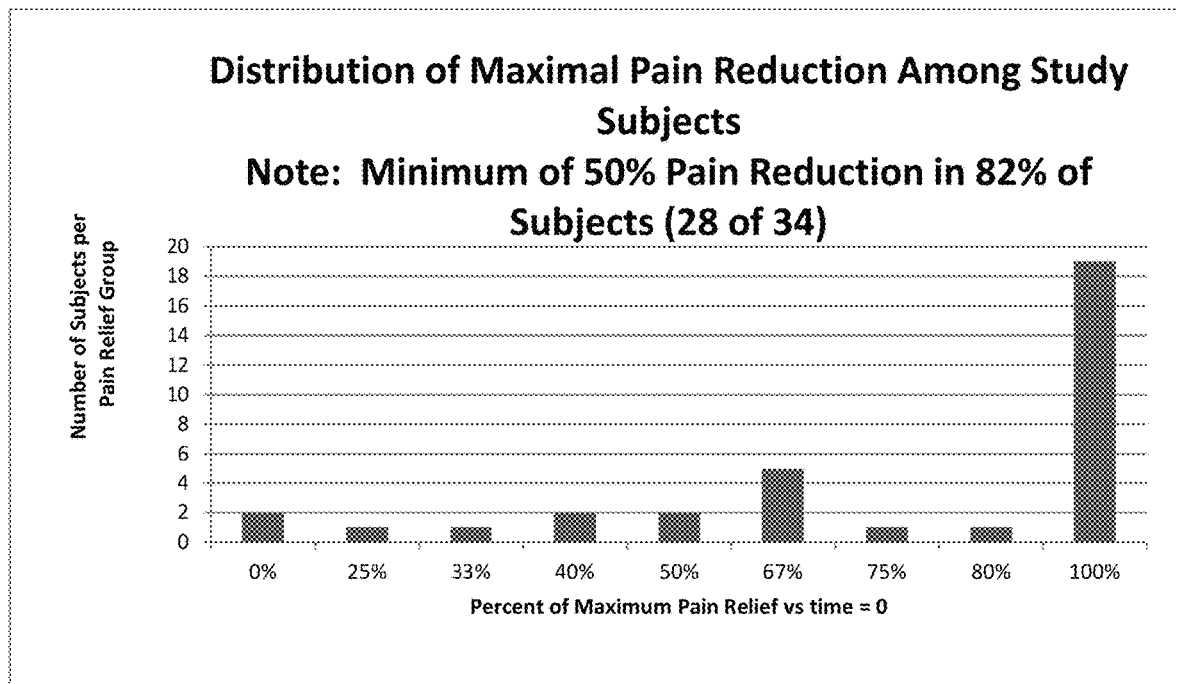
FIG. 6 shows the maximal pain reduction for the study subjects.

Related to the individual reduction in pain is the extent of pain reduction, based on the initial score. This analysis groups the cohort by percent of pain reduction, asking how many subjects experienced various level of pain relief. As indicated in FIG. 6, many subjects experienced a high level of pain relief, with a total of 28 of 34 subjects having relief at 50% or better.

Figure 7:
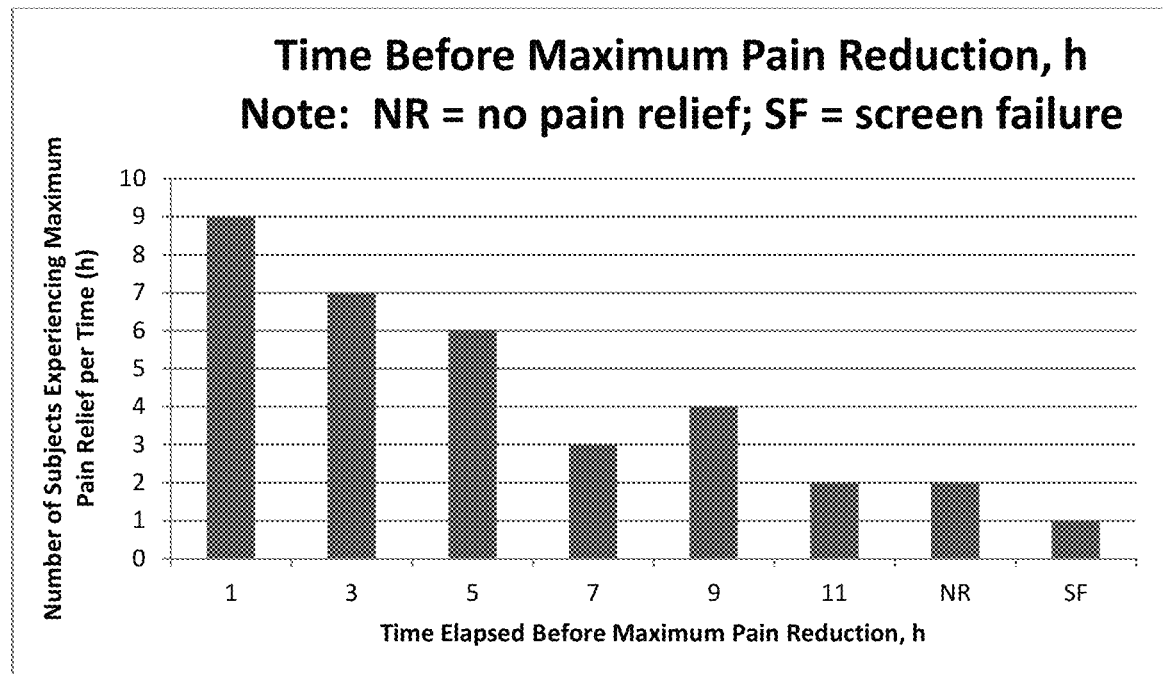
FIG. 7 shows the time of maximum pain relief for the study subjects.

Effect latency, or the time before maximum pain relief, was another measure of interest. Again, there are inter-subject variables that may impact the time before maximum pain effect. Indeed, having 2 doses of lidocaine imposes on each subject 2 pharmacokinetic curves that may, in some individuals and depending on the time between dosing, be additive. Nonetheless, it is instructive that 9 subjects expressed maximum pain relief at the 1 hour point, with the extent of relief presenting an almost exponential decay following that point (FIG. 7).

Conclusion

Thirty-four subjects were enrolled (20 women, 14 men). Prior to drug administration, neither lidocaine nor MEGx was found in the serum of any of the subjects. Serum concentrations for both analytes were below the limit of detection for the analytical method (0.1 mcg/mL), with the exception of one male subject, whose 5-hour MEGx level was reported as detectable at the detection limit of 0.1 mcg/m L. Possible adverse reactions among study subjects, which included central nervous system and cardiovascular effects, were not reported. Initial self-reported acute pain levels by VAS ranged from 1 to 8, with a mean (+/−SD) prior to drug administration of 4.33(1.72); pain levels subsequent to lidocaine application were at 1 h: 2.33(1.8); 3 h: 2.14 (2.16); 5 h: 1.88(2.09); 7 h: 1.73(2.29); 9 h: 1.67(2.23); and 11 h: 2.07(1.69). The study population achieved reductions in the initial level of acute pain of 41% (1 h), 54% (3 h), 59% (5 h), 64% (7 h), 62% (9 h) and 57% (11 h). Pain reduction was 50% or greater among 82% of subjects (28 of 34), with the time elapsed to reach maximal pain reduction being 1 h for 27% of subjects, followed by 21% (3 h), 18% (5 h), 9% (7 h), 12% (9 h), and 6% (11 h).

This Phase 1 study provides direct evidence demonstrating the safety of NeuroMed7™ 4% lidocaine cream when used as indicated in the OTC monograph, ie, 1 mL dosing at least 4 h apart, with a maximum of 2 doses per day. No sufficiently high blood levels of lidocaine or MEGx that would indicate toxicity was detected, and there were no reported clinical signs of overdose. Our analysis of efficacy demonstrated positive responses whose broad variation is attributed to the locus of pain and pain history, as well as other uncontrolled variables. Despite the spread in response, the use of NeuroMed7™ as indicated provides effective topical pain relief, while presenting little in the way of secondary adverse effects. Lidocaine is an agent that can be physiologically damaging at doses much higher than used in this study. However, when used as indicated, NeuroMed7™ provides a broad margin of safety to the user.

Thus the lidocaine formulation presented no measurable safety issues, either in measureable serum levels (since the highest measurable level was 0.10 mcg/mL, whereas toxicity is indicated at >5 mcg/mL), or in physiological response, and was effective among the majority of these subjects.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A topical delivery system comprising a pharmaceutical composition formulated for application directly to a skin of a subject in need thereof comprising:
   (a) a therapeutic amount of an amino benzoate local anesthetic agent;
   (b) chemical drivers comprising ethoxydiglycol, propylene glycol and methylsulfonylmethane (MSM), wherein the chemical drivers are cooperatively effective to deliver the amino benzoate local anesthetic agent into skin;
   (c) a depot component comprising a polymer for encapsulation of the pharmaceutical composition, and
   (d) a stabilizer,
wherein the depot component keeps the active agent locally in the skin and reduces distribution of the active agent to the blood stream.

2. The topical delivery system according to claim 1, wherein the depot component comprises an emollient and a surfactant.

3. The topical delivery system according to claim 2, wherein the polymer is polyacrylamide (1-20% w/w), the emollient is $C_{13-14}$ isoparaffin (1-20% w/w), and the surfactant is laureth-7 (1-20% w/w).

4. The topical delivery system according to claim 3, wherein the depot component is formed by the polyacrylamide polymer, the $C_{13-14}$ isoparaffin emollient and the laureth-7 surfactant.

5. The topical delivery system according to claim 1, wherein the active therapeutic agent has a molecular weight below 500 Da.

6. The topical delivery system according to claim 1, wherein the local anesthetic is selected from the group consisting of benzocaine, lidocaine, tetracaine or a combination thereof.

7. The topical delivery system according to claim 1, wherein the pharmaceutical composition is in an administration form selected from the group consisting of a cream, gel, or a spray.

8. The topical delivery system according to claim 1, further comprising a vasoconstrictor.

9. The topical delivery system according to claim 8, wherein the vasoconstrictor is nonirritating when applied to skin.

10. A method of delivering a pharmaceutical composition topically that is effective to reduce systemic side effects of the active agent comprising:
   (a) applying a pharmaceutical composition to a skin of a subject in need thereof, wherein the pharmaceutical composition comprises:
      (i) a therapeutic amount of an amino benzoate local anesthetic agent;
      (ii) chemical drivers comprising ethoxydiglycol, propylene glycol and methylsulfonylmethane (MSM), wherein the chemical drivers are cooperatively effective to deliver the amino benzoate local anesthetic agent into skin;
      (iii) a depot component comprising a polymer, and
      (iv) a stabilizer,
   wherein the depot component encapsulates the pharmaceutical composition; keeps the aminobenzoate local anesthetic agent locally in the skin; and reduces distribution of the active agent to the blood stream.

11. The method according to claim 10, wherein the depot component comprises an emollient and a surfactant.

12. The method according to claim 11, wherein the polymer is polyacrylamide (1-20% w/w), the emollient is $C_{13-14}$ isoparaffin (1-20% w/w), and the surfactant is laureth-7 (1-20% w/w).

13. The method according to claim 12, wherein the polyacrylamide polymer, the $C_{13-14}$ isoparaffin emollient and the laureth-7 surfactant form the depot component.

14. The method according to claim 10, wherein the active therapeutic agent has a molecular weight below 500 Da.

15. The method according to claim 10, wherein the amount of the therapeutic agent in the blood stream is less than a therapeutic amount.

16. The method according to claim 10, wherein the depot component facilitates controlled or delayed type release of the active therapeutic agent.

* * * * *